(12) United States Patent
Bartling

(10) Patent No.: US 12,079,309 B2
(45) Date of Patent: Sep. 3, 2024

(54) FORECAST REVISION

(71) Applicant: Arm Limited, Cambridge (GB)

(72) Inventor: Michael Bartling, Austin, TX (US)

(73) Assignee: Arm Limited, Cambridge (GB)

( * ) Notice: Subject to any disclaimer, the term of this patent is extended or adjusted under 35 U.S.C. 154(b) by 243 days.

(21) Appl. No.: 17/559,246

(22) Filed: Dec. 22, 2021

(65) Prior Publication Data

US 2023/0195846 A1 Jun. 22, 2023

(51) Int. Cl.
*G06F 17/00* (2019.01)
*A61B 5/145* (2006.01)
(Continued)

(52) U.S. Cl.
CPC ...... *G06F 18/2193* (2023.01); *A61B 5/14532* (2013.01); *G06F 11/3409* (2013.01);
(Continued)

(58) Field of Classification Search
CPC ............ G06N 20/00; G06N 3/08; G06N 7/01; G06N 3/045; G06N 3/047; G06N 20/20; G06N 3/09; G06N 3/0895; G06N 3/0455; G06N 3/02; G06F 17/18; G06F 18/2178; G06F 16/285; G06F 30/27; G06F 16/906; G06F 16/355; G06F 16/35; G06F 18/24; G06F 18/24133; G06F 18/24137; G06F 18/2414; G06F 18/24143; G06F 18/24147; G06F 18/2413; G06F 18/2415; G06F 18/24155; G06F 18/254; G06F 18/25; G06F 9/4401; G06F 16/55; G06F 7/14; G06F 18/23; G06F 18/24323; G06F 18/243; G06F 18/2431; G06F 18/24317; G06F 18/2433; G06F 18/241; G06F 18/2411;
(Continued)

(56) References Cited

U.S. PATENT DOCUMENTS

2016/0350671 A1* 12/2016 Morris, II .......... G05B 23/0229
2019/0049968 A1* 2/2019 Dean ........................ A61G 5/04
(Continued)

FOREIGN PATENT DOCUMENTS

EP 3813034 A1 * 4/2021 ............. G08G 1/096

OTHER PUBLICATIONS

Search machine translation of Kai et al., EP-3813034-A1, translated Oct. 16, 2023, 12 pages. (Year: 2023).*
(Continued)

*Primary Examiner* — Matthew C Bella
*Assistant Examiner* — Dennis Rosario
(74) *Attorney, Agent, or Firm* — NIXON & VANDERHYE P.C.

(57) ABSTRACT

A data processing apparatus is provided that includes forecast circuitry for generating a forecast of an aspect of a system for a next future time and for one or more subsequent future times following the next future time. Measurement circuitry generates, at the next future time, a new measurement of the aspect of the system. Aggregation circuitry produces an aggregation of the forecast of the aspect of the system for the next future time and of the new measurement of the aspect of the system. The forecast circuitry revises the forecast of the aspect of the system for the one or more subsequent future times using the aggregation.

18 Claims, 18 Drawing Sheets

(51) Int. Cl.

| | |
|---|---|
| *G06F 11/34* | (2006.01) |
| *G06F 17/18* | (2006.01) |
| *G06F 18/21* | (2023.01) |
| *G06Q 30/0202* | (2023.01) |
| *A61B 5/02* | (2006.01) |
| *A61B 5/24* | (2021.01) |
| *G06F 16/906* | (2019.01) |
| *G06N 20/00* | (2019.01) |
| *G06Q 30/02* | (2023.01) |
| *G06V 10/774* | (2022.01) |

(52) U.S. Cl.
CPC .......... *G06F 11/3452* (2013.01); *G06F 17/00* (2013.01); *G06F 17/18* (2013.01); *G06Q 30/0202* (2013.01)

(58) Field of Classification Search
CPC .......... G06F 2218/12; G06F 18/24765; G06F 11/00; G06F 3/0418; G06F 16/217; G06F 17/00; G06F 17/10; G06F 11/3409; G06F 11/3419; G06F 11/3428; G06F 11/3433; G06F 11/3414; G06F 11/3452; G06F 11/34; G06F 16/24556; G06F 18/27; G06V 10/70; G06V 10/7784; G06V 10/82; G06V 10/764; G06V 40/172; G06V 10/761; G06V 10/74; G06V 10/7625; G06V 10/762; G06V 10/774; G06V 10/80; G06V 10/809; G06V 10/811; G06V 10/84; G06V 10/87; G06V 20/698; G06V 30/19173; G06V 10/7788; G06V 30/1918; G06V 30/2552; G06V 20/70; G06V 30/19167; G06V 30/19107; G06V 30/413; G06V 40/197; A61B 5/7267; A61B 5/7264; A61B 5/0006; A61B 5/14532; A61B 5/145; A61B 5/7275; A61B 5/01; A61B 5/021; A61B 5/02; A61B 5/24; A61B 5/369; A61B 5/28; A61B 5/318; H02J 3/003; H02J 3/004; G06T 2207/20081; G06T 2207/20084; G06T 11/206; G06T 2207/30242; G06T 2207/20076; G06T 9/002; G06T 2219/004; G06T 2207/20221; G06T 7/0012; G06T 2207/30004; G08G 1/0133; B60W 30/0956; B60W 50/0097; B60W 30/095; G10L 15/063; G10L 15/06; G10L 2015/0631; G10L 15/16; G10L 15/08; G10L 25/30; G10L 15/144; G10L 17/18; G01C 21/3617; C12Q 2600/158; G16H 50/20; G16H 50/50; G16H 50/00; G16H 50/30; G16B 40/00; G01N 33/57407; G06Q 30/0201; G06Q 30/0202; G06Q 30/0203; G06Q 30/0283; G06Q 30/0204; G06Q 50/16; G06Q 40/00; G06Q 40/04; G06Q 40/03; G06Q 30/02; G06Q 30/0206; G06Q 10/04; G06Q 30/06; G06Q 30/0645; G06Q 30/0278

See application file for complete search history.

(56) References Cited

U.S. PATENT DOCUMENTS

| | | | |
|---|---|---|---|
| 2022/0239122 A1* | 7/2022 | Baumann | B60L 58/26 |
| 2022/0398492 A1* | 12/2022 | Navon | G06F 18/214 |
| 2023/0196854 A1* | 6/2023 | Lopez De La Cruz | ............... B60C 11/246 701/29.4 |

OTHER PUBLICATIONS

U.S. Appl. No. 63/291,494: Tire Replacement System for Cruz et al., US 2023/0196854 A1, Dec. 20, 2021 [retrieved Oct. 16, 2023], 19 pages. (Year: 2021).*

Drawings for U.S. Appl. No. 63/291,494: Tire Replacement System for Cruz et al., US 2023/0196854 A1, Dec. 20, 2021 [retrieved Oct. 16, 2023], 10 pages. (Year: 2021).*

Du et al., Putting the "Learning" into Learning-Augmented Algorithms for Frequency Estimation, Jul. 18-24, 2021 [retrieved Oct. 16, 2023], Proceedings of the 38th International Conference on Machine Learning, vol. 139, 10 pages. Retrieved: https://proceedings.mlr.press/v139/ (Year: 2021).*

Hyndman et al., Forecasting: Principles and Practice, Sep. 5, 2018 [retrieved Oct. 16, 2023], 2nd Edition, 504 pages. Retrieved : https://scholar.google.com/scholar?cluster=7175699242473531713&hl=en&as_sdt=0,47 (Year: 2018).*

Steenbergen et al., A non-parametric data-based approach for probabilistic flood forecasting in support of uncertainty communication, Feb. 21, 2012 [retrieved Apr. 18, 2024], Environmental Modeling & Software, vol. 33, pp. 92-105. Retrieved: (Year: 2012).*

[Item U continued] https://www.sciencedirect.com/science/article/pii/S136481521200031X (Year: 2012).*

U.S. Appl. No. 17/559,202, filed Dec. 22, 2021, Bartling et al.

Park, et al., "A Multimodal Anomaly Detector for Robot-Assisted Feeding Using an LSTM-based Variational Autoencoder", IEEE Robotics and Automation Letters, vol. 3, No. 3, Jul. 2018, pp. 1544-1551 (8 pp.).

Yang, et al., "Conditional Variational Auto-Encoder and Extreme Value Theory Aided Two-Stage Learning Approach for Intelligent Fine-Grained Known/Unknown Intrusion Detection", IEEE Transactions on Information Forensics and Security, vol. 16, 2021, pp. 3538-3553 (16 pp.).

Conference Paper: Cormode, et al., "An Improved Data Stream Summary: The Count-Min Sketch and its Applications", Conference: LATIN 2004: Theoretical Informatics, 6th Latin American Symposium, Buenos Aires, Argentina, Apr. 5-8, 2004, Proceedings, Jan. 2004, 12 pp.

Hyndman, et al., "Forecasting: Principles and Practice ($2^{nd}$ ed)", 3.5 Prediction intervals, Apr. 2018, 6 pp., URL: https:otexts.com/fpp2/prediction-intervals.html.

Shukla, et al., "Big Data with sketchy Structures, Part 1-the Count-Min Sketch", website: towards data science, Jul. 17, 2018, 9 pp., URL: https://towardsdatascience.com/big-data-with-sketchy-structures-part-1-the-count-min-sketch-b73fb3a33e2a.

Paper: Cho, et al., "Learning Phrase Representations using RNN Encoder-Decoder for Statistical Machine Translation", Empirical Methods in Natural Language Processing, Sep. 3, 2014, 15 pp., arXiv:1406.1078v3 [cs.CL] Sep. 3, 2014.

Zhang, et al., "On the Properties of Kullback-Leibler Divergence Between Gaussians", Feb. 10, 2021, 35 pp., arXiv:2102.05485v3 [cs.IT] May 27, 2021.

Accepted Research Paper: Jiang, et al., "SketchML: Accelerating Distributed Machine Learning with Data Sketches", The 2018 ACM SIGMOD/PODS Conference: Houston, USA—SIGMOD Accepted Research Papers, SIGMOD '18, Jun. 10-15, 2018, Houston, TX, US, 16 pp.

\* cited by examiner $t_0$     Prediction for $\omega_1$     Prediction for $\omega_2$     Prediction for $\omega_3$
       [ 7, 15, 4 ],        [ 0, -1, -3 ],        [ 6, 13, 27 ]

$t_1$     Measurements for $\omega_1$
       [ 6, 15, 9 ]

Aggregation for $\omega_1$ $$\left[ \frac{7+6}{2}, \frac{15+15}{2}, \frac{4+9}{2} \right] = \left[ 6.5, 15, 6.5 \right]$$

Revised prediction for $\omega_2$     Revised prediction for $\omega_3$     Prediction for $\omega_4$
[ -0.5, -1, -1 ]        [ 5.5, 13, 28 ]        [ -2, -7, 1 ]

FIG. 13

$t_0$     Prediction for $\omega_1$     Prediction for $\omega_2$     Prediction for $\omega_3$
      [ 7, 15, 4 ],       [ 0, -1, -3 ],       [ 6, 13, 27 ]

$t_1$     Measurements for $\omega_1$
      [ 6, 15, 9 ]

Aggregation for $\omega_1$ $$\left[\frac{7+3(6)}{4}, \frac{15+3(15)}{4}, \frac{4+3(9)}{4}\right] = \left[6.25, 15, 7.75\right]$$

Revised prediction for $\omega_2$     Revised tprediction for $\omega_3$     Prediction for $\omega_4$
[ -0.75, -1, 0 ]       [ 6, 13, 29 ]       [ -2.5, -7, 1.5 ]

FIG. 14

FORECAST REVISION

TECHNICAL FIELD

The present disclosure relates to data processing.

DESCRIPTION

It is desirable for machine learning systems to be able to improve the quality of predictions (e.g. the forecast and/or the confidence) that are made.

SUMMARY

Viewed from a first example configuration, there is provided a data processing apparatus comprising: forecast circuitry configured to generate a forecast of an aspect of a system for a next future time and for one or more subsequent future times following the next future time; measurement circuitry configured to generate, at the next future time, a new measurement of the aspect of the system; and aggregation circuitry configured to produce an aggregation of the forecast of the aspect of the system for the next future time and of the new measurement of the aspect of the system, wherein the forecast circuitry is configured to revise the forecast of the aspect of the system for the one or more subsequent future times using the aggregation.

Viewed from a second example configuration, there is provided a data processing method comprising: generating a forecast of an aspect of a system for a next future time and for one or more subsequent future times following the next future time; generating, at the next future time, a new measurement of the aspect of the system; producing an aggregation of the forecast of the aspect of the system for the next future time and of the new measurement of the aspect of the system; and revising the forecast of the aspect of the system for the one or more subsequent future times using the aggregation.

Viewed from a third example configuration, there is provided a non-transitory computer-readable medium to store computer-readable code for fabrication of a data processing apparatus comprising: forecast circuitry configured to generate a forecast of an aspect of a system for a next future time and for one or more subsequent future times following the next future time; measurement circuitry configured to generate, at the next future time, a new measurement of the aspect of the system; and aggregation circuitry configured to produce an aggregation of the forecast of the aspect of the system for the next future time and of the new measurement of the aspect of the system, wherein the forecast circuitry is configured to revise the forecast of the aspect of the system for the one or more subsequent future times using the aggregation.

BRIEF DESCRIPTION OF THE DRAWINGS

The present invention will be described further, by way of example only, with reference to embodiments thereof as illustrated in the accompanying drawings, in which:

FIG. 13 shows an example of the aggregation process;

FIG. 14 shows an example of the aggregation process;

DESCRIPTION OF EXAMPLE EMBODIMENTS

Figure 1:
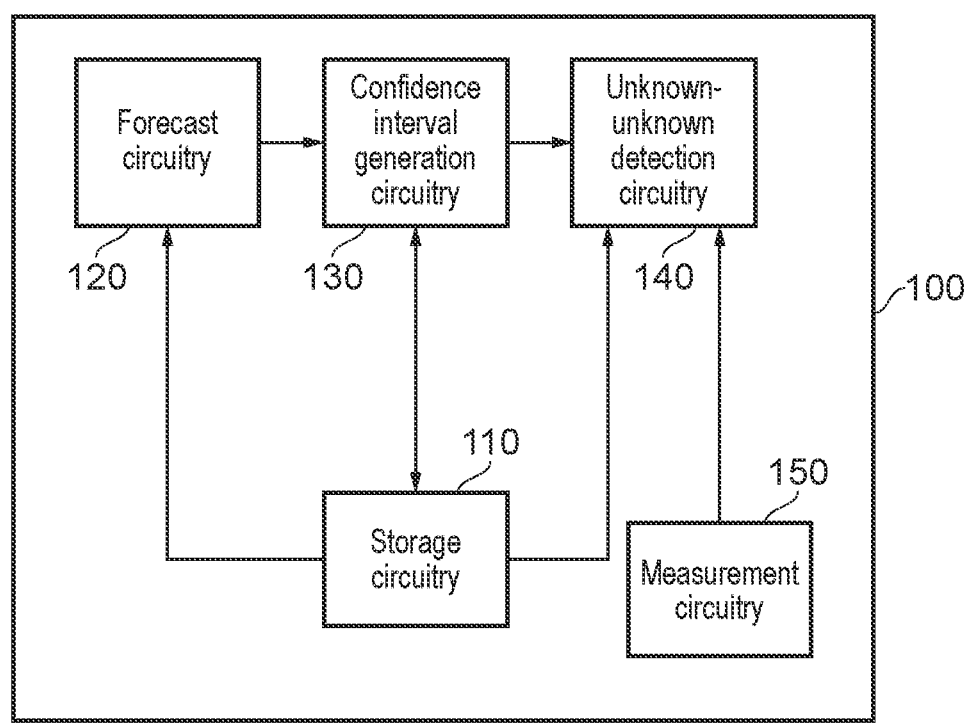
FIG. 1 illustrates a data processing apparatus in accordance with some embodiments.

Before discussing the embodiments with reference to the accompanying figures, the following description of embodiments is provided.

In accordance with one example, there is provided a data processing apparatus comprising: forecast circuitry configured to generate a forecast of an aspect of a system for a next future time and for one or more subsequent future times following the next future time; measurement circuitry configured to generate, at the next future time, a new measurement of the aspect of the system; and aggregation circuitry configured to produce an aggregation of the forecast of the aspect of the system for the next future time and of the new measurement of the aspect of the system, wherein the forecast circuitry is configured to revise the forecast of the aspect of the system for the one or more subsequent future times using the aggregation.

The forecast circuitry is used to produce a forecast in respect of a next future time (e.g. a next window of time) and one or more times after that. The forecast circuitry therefore produces a plurality of forecasts. The forecasts are made in the form of a time series. When the time reaches the next future time, a measurement is taken. This can then be compared to the forecast that was produced. Aggregation circuitry is used to aggregate the measurement with the corresponding forecast thereby producing an aggregation. That is to say that the forecast that was provided for a point in time is modified by the actual measurement that is taken for that point in time. The result of this aggregation is then used by the forecast circuitry to amend the remaining forecasts (specifically for the one or more subsequent future times). Since the forecast is being made based on the aggregation, which is itself a modified previous forecast, revised forecast can taken into account not only what was previously predicted but also what the actual measurement turned out to be. A degree of tuning can therefore be performed. If the actual measurements turn out to be different (in a reliable manner) from the forecasts, then this can be taken into account for the future forecasts. This is achieved by the aggregation of the previous forecast and the measurement. Consequently, as time goes on, the tuning should reflect confidence in predictions based on historical measurements; as confidence improves the accuracy of prediction has stronger guarantees, and as confidence degrades so do the guarantees in prediction accuracy. Note that, as described below, the new measurement need not be from a sensor or be 'live' data from the system.

In some examples, the aggregation is an average between the forecast of the aspect of the system for the next future time and between the new measurement of the aspect of the system. For instance, the aggregation could be the mean of the measurement at a point in time and a previous forecast for that point in time. The forecast can therefore be smoothed according to actual measurements.

In some examples, the aggregation is a weighted average between the forecast of the aspect of the system for the next future time and between the new measurement of the aspect of the system; and each of weights applied to the forecast of the aspect of the system for the next future time and between the new measurement of the aspect of the system are different and non-zero. Each of the two values (the measurement and the corresponding previous prediction) can be weighted by a different amount. In other words, each of the two values can be multiplied by a different weight, the results added together and then divided by the total weight. This allows one of the actual measurement or the forecast to be considered to be more important than the other, and to therefore have a bigger impact on the revised forecast than the other.

In some examples, the aggregation is a weighted average between the forecast of the aspect of the system for the next future time and between the new measurement of the aspect of the system; and each of weights applied to the forecast of the aspect of the system for the next future time and between the new measurement of the aspect of the system are different, and greater than zero.

In some examples, the next future time and each of the subsequent future times are windows of time. Windows may be for fixed periods of time (e.g. 20 ms each), during which the aspect of the system could change a number of times. During each window of time, a (fixed) number of measurements might be made.

In some examples, the measurement circuitry is configured to generate, at the next future time, a plurality of new measurements of the aspect of the system including the new measurement; the aggregation circuitry is configured to produce the aggregation by aggregating corresponding pairs of values; and each of the pairs of values has a first value associated with the forecast of the aspect of the system for the next future time and a second value associated with the new measurement of the aspect of the system. In these examples, a plurality of measurements are made during each window. The aggregation that occurs is between a measurement of the current window and a corresponding previous forecast for the current window. That is, if three measurements/forecasts are made for each window then a first aggregation will be performed in respect of the first values of the forecast/measurement, a second aggregation will be performed in respect of the second values of the forecast/measurement, and a third aggregation will be performed in respect of the third values of the forecast measurement. The overall aggregation would therefore consist of three separately aggregated values.

In some examples, the data processing apparatus comprises circular buffer circuitry to store the forecast of the aspect of the system for the next future time and for the one or more subsequent future times following the next future time. A circular buffer can be considered to be a form of storage circuitry in which the head of a list can be started at any position within the buffer with the end of the buffer wrapping around to the front of the buffer. Thus, if the buffer stores n items and the head of the list is at a position m (m>0) then the tail of the list is found at position m−1 (in the case of m=0, the tail is found at position n). In the present examples, new items are added to the circular buffer by replacing the oldest item in the buffer and potentially zeroing out or reinitializing on overwrite.

In some examples, the aggregation circuitry is configured to replace the forecast of the aspect of the system for the next future time with the aggregation. Modifications/revisions are made to the forecast 'in-place' thereby obviating the need for additional buffers or storage circuitry to store new measurements for more than one cycle.

In some examples, the data processing apparatus residual calculation circuitry configured to calculate residuals of the forecast of the aspect of the system for the next future time and for the one or more subsequent future times following the next future time; and confidence interval generation circuitry configured to generate, for each forecast of the aspect of the system and for the one or more subsequent future times following the next future time, confidence intervals based on the residuals. A residual can be considered to be a difference between a forecast and a 'ground truth', e.g. a measurement taken for the window for which the forecast was produced. Essentially a residual can be used to give an error for the forecast. By considering the residuals, it is possible to give an indication of the confidence intervals for a forecast. For instance, if residuals are large, then the confidence are likely to be large and vice-versa.

In some examples, the confidence intervals are generated so as to encompass forecasts whose residuals fall within a predefined percentile. For instance, the confidence intervals might be selected so that the $95^{th}$ percentile of residuals aggregated with a measurement or forecast are encompassed within the space defined by the confidence intervals. This makes it possible to exclude anomalous outlying data points.

In some examples, the data processing apparatus comprises min-sketch circuitry configured to perform min-sketch using the residuals to approximate the predefined percentile. Min-sketch is a technique that makes it possible to estimate (functions or aggregations) on a list of values without having to store the entire list of values. For instance, it will be appreciated that in order to determine a median value of a list of data, it is necessary to store the list of data items. With min-sketch, it is possible to achieve a good estimate of the median value without the entire list of data items being stored. This technique therefore makes it possible to determine forecasts falling within a given percentile (e.g. the $95^{th}$ percentile) in a changing list of forecasts, without all of those forecasts having to be stored.

In some examples, the forecast circuitry is configured to generate the forecast for the next future time and for the one or more subsequent future times following the next future time, for each of a plurality of classes. A class can be thought of as a category associated with a particular set of data (usually in a categorisation problem). For instance, a forecast might be made for a first time series for the performance of a computer system operating with malware while a second forecast might be made for a second time series for the performance of the same computer system operating with benignware. Here, the classes would be "with malware" and "with benignware".

In some examples, the data processing apparatus comprises distance circuitry configured to determine a measurement of distance between the new measurement and the confidence interval for each of the plurality of classes, wherein the measurement is lower when the new measurement is nearer or within the confidence interval and higher when the new measurement is further or outside the confidence interval. The measurement circuitry can therefore be used to determine how far a given measurement is for a particular class and its confidence interval (e.g. how far away a measurement is from the confidence in a prediction given historical context). The distance circuitry can therefore be used to give an indication of how far away a measurement is for possible behaviour of a particular class (or indeed, for each class).

In some examples, the data processing apparatus comprises unknown-unknown circuitry configured to label the new measurement as an unknown-unknown in response to the measurement of the distance between the new measurement and the confidence interval for each of the plurality of classes being above a threshold. An unknown-unknown can be defined as a measurement that occurs sufficiently far outside any of the confidence intervals for the different classes (e.g. above the threshold).

In some examples, the distance circuitry is configured to calculate the area encompassed by each confidence interval. Large confidence areas indicate a greater degree of unknown about future forecasts (e.g. that the forecasts are not considered to be particularly accurate).

In some examples, the unknown-unknown circuitry is configured to label the new measurement, which is an unknown-unknown, as belonging to an unknown new class other than the classes in response to the area being above a threshold value. A new value might be an unknown-unknown for a variety of reasons. In some situations, the value might be an unknown-unknown because the forecasts are not particularly accurate—represented by the fact that the confidence interval area is large. In these situations, the new measurement could belong to a previously unknown class. For instance, in the previous examples of classes including "with malware" and "with benignware", the new class could represent a different situation that is neither of these two scenarios such as "with spyware", which could be considered to be neither malware nor entirely benign.

In some examples, the unknown-unknown circuitry is configured to label the new measurement, which is an unknown-unknown, as a special case of one of the classes in response to the area being below a threshold value. Where the confidence interval area is below a threshold value (e.g. small) the forecasts are generally well defined and thus the classes are well-known. In this situation, it is less likely that a new measurement represents a previously unknown class and instead in these situations, the unknown-unknown could represent a previously unknown situation (e.g. a special case) of one of the existing classes. Again taking the previously presented classes, this could represent a new strain of malware, for instance.

In some examples, the new measurement of the aspect of the system is part of a set of training data. The new measurement therefore need not be produced from a sensor, but could be part of training data that is used to train a system.

The following example configurations may also be relevant to the present disclosure:

In accordance with one example configuration there is provided a data processing apparatus comprising: storage circuitry to store a plurality of future time series forecasters of an aspect of a system and, for each of the future time series forecasters, a representation of a confidence interval associated with that future time series forecaster; and unknown-unknown detection circuitry configured to determine whether a new measurement falls outside confidence intervals generated from the representation of the confidence interval associated with each future time series forecaster of the aspect of the system, and in response to the new measurement falling outside the confidence intervals, to label the new measurement as an unknown-unknown.

The future time-series forecasters are used to forecast an aspect of a system. Examples of these aspects and systems could include a performance of a computer, an ECG of a patient, a variant in house price, or another aspect of a system where a given value of the aspect is dependent on a previous value in the time series. One example of a forecaster could be, for instance, a linear regressor. Often, the forecasters have been trained using machine learning and a set of training data. In these situations, an unknown-unknown could represent a data value that was not part of the training data (or one that was in the training data, but was not used to generate a forecaster). A confidence interval can be used to indicate not merely the predicted value but a range of likely values. That is the confidence interval might allow one to say that the expected value would fall within the confidence interval with a given degree of certainty. The representation of that confidence interval could be the actual confidence interval itself or could be a simplification of the confidence interval that can be stored in a smaller amount of storage space. The unknown-unknown detection circuitry determines that a given measurement is an unknown-unknown if it falls outside the confidence intervals since this represents the situation in which the data has (probably) not been taken into account in the development of the forecasters. Each set of historical measurements can be used to generate a different forecaster for the aspect of the system. That is, each set of measurements may be associated with a different class or category. In the case of ECGs for instance, one set of historical data could be used for "patients experiencing heart attacks", another set could be used for "normal healthy patients", and another set of historical data could be used for "patients with arrhythmia". Each of the forecasters can therefore be associated with a different such class. In some examples, when the unknown-unknown is labelled as such, an exception is raised so as to alert the user.

In some examples, the data processing apparatus comprises: second storage circuitry configured to store a plurality of sets of historical measurements of the aspect of a system; forecast circuitry configured to generate, for each set of historical measurements, the future time series forecaster of the aspect of the system; and confidence interval generation circuitry configured to generate, for each future time series forecast of the aspect of the system, the confidence interval of the future time series forecast of the aspect of the system. These examples include historical data which can be used as a basis of the training data used to generate the future time series forecasters for the aspect of the system. For instance, the historical data could be performance data for a computer running malware while carrying out a set of activities and performance data for a computer not running malware while carrying out the same set of activities. From the future time series forecasts, an actual confidence interval can be determined (as opposed to a simplified representation). This can be used to generate the confidence interval representation either by simplifying the confidence interval or by using the confidence interval as its own representation. The second storage circuitry could be the same or different to the previously mentioned storage circuitry.

In some examples, each set of historical measurements in the sets of historical measurements is a time series.

In some examples, the confidence interval generation circuitry is configured to generate, for each future time series forecaster of the aspect of the system, the confidence interval of the aspect of the system by using bootstrapping. Bootstrapping can be considered to be a process in which previous historic values are used to estimate possible futures of a system. Taking the example of an ECG, which measures voltage over time, random windows of the previous behaviour of the system (e.g. each of 0.25 s) could be taken. Starting from a current voltage value, these could be combined in order to illustrate a possible future behaviour of the system. The average across several such future forecasts could be used to establish a most-likely average prediction for the aspect of the system.

In some examples, the confidence interval generation circuitry is configured to generate the representation of the confidence interval from boundaries of a plurality of future time series forecasts of the aspect of the system. The bootstrapping process can therefore be performed many times (e.g. 1,000,000) times, each representing a different possible future. The boundaries of those time series therefore collectively represent the confidence interval, since it would be likely for any future of the behaviour to fall within the boundaries of those forecasts. In some examples, the confidence interval is taken by considering some percentage of the time series so as to avoid outliers. For instance, the confidence intervals might be placed to encompass 95% of the forecasts, the $95^{th}$ percentile.

In some examples, the confidence interval generation circuitry is configured to generate the representation of the confidence interval from the confidence interval via distillation. The representation of the confidence interval could therefore be determined statistically, e.g. by considering where the $95^{th}$ percentile of the future forecasts lie at each point in time on the time series. The representation of the confidence interval could be represented by considering the statistics (e.g. the standard deviation and mean) of the residual error—that is the statistics of the difference between the average of the forecasts and the confidence interval of the forecasts (optionally including a small fixed error or epsilon). The confidence interval representation might be a tuple consisting of, at each point in time (or at each window), a mean and a standard deviation.

In some examples, the new measurement is absent from the sets of historical measurements. By performing unknown-unknown detection on a previously unknown measurement (e.g. one that was not used to generate the future time series forecasters) it is possible to detect the presence of measurements for which the forecasters may not be well equipped to handle (having not been trained on such data). Where the future forecasters are used in categorisation tasks, this might represent a new category. For instance, where future forecasters are used to categorise whether a computer system is running malware, future forecasters might have been built for a system that "has malware" and "does not have malware". The presence of a new data point outside the confidence intervals of these forecasts could represent a new category or class corresponding, for instance "spyware". Alternatively, this could represent a new type of malware that was previously not seen and that therefore is not represented or handled by the current forecasters. The new measurement could also be present in the historical measurements. This may be the case where a random subsets of data are randomly selected for a large set of historical data in order to form a forecaster (as can happen with bootstrapping and more generally for most model validation schemes used in machine learning such as k-fold validation for instance). Here, the detection of an unknown-unknown might be indicative that the forecaster is unsuitable for use or that the subsets of data being used for random sampling are too small.

In some examples, in response to the new measurement being labelled as the unknown-unknown, the new measurement is added to one of the plurality of sets of historical measurements. In response to discovering a new measurement that is an unknown-unknown, the new measurement can be added to one of the historical measurement sets in order to improve training of the forecasters in the future.

In some examples, in response to the new measurement being labelled as the unknown-unknown, the new measurement is added to a new set of historical measurements. In these situations, the new measurement could be considered to be a new class or category of measurement (using some of the above examples: the presence of spyware on a machine rather than malware or nothing at all).

In some examples, the representation of the confidence interval is generated by random sampling of the confidence interval. By taking random samples of the confidence interval, the representation can be generated by considering, for instance, a mean and a standard deviation of the residual error (explained above).

In some examples, the forecast circuitry is configured to generate, as the future time series forecaster of the aspect of the system and the confidence interval generation circuitry is configured to generate, as the confidence interval of the future time series forecast of the aspect of the system, probability distributions generated based on the historical measurements of the aspect of the system; and the unknown-unknown detection circuitry is configured to determine a distance between a test distribution and the probability distributions and in response to the distance between the test distribution and the probability distributions exceeding a threshold, to determine that the test probability distribution represents an unknown-unknown. A distribution of historical measurements of an aspect of a system can act as both a forecaster and a representation of a confidence interval (by providing the same statistical criteria). If these distributions are significantly different to a test distribution generated for a set of measurements then the set of measurements can be said to not belong to that distribution. Where a distribution or set of distributions are provided for each class, then if the test distribution differs from all the distributions, then it could be considered to be an unknown-unknown. In some of these examples, the probability distributions are generated using a variational autoencoder based on the historical data. The distance can be calculated, for instance, using KL divergence.

In some examples, the data processing apparatus comprises: forecast circuitry configured to generate future time series forecasts of the aspect of the system from the plurality of future time series forecasters; and estimated confidence interval generation circuitry configured to generate, for each future time series forecast of the future time series forecasts, the confidence interval of that future time series forecast using the representation of the confidence interval associated with that future time series forecast, wherein the confidence interval is an estimated confidence interval. In these examples, the forecasters are used to generate forecasts, and the confidence intervals (which are estimates of the confidence interval) are generated from the representations of the confidence interval. For instance, if the representation of the confidence interval provides a mean and standard deviation then this can be used to produce an estimated (probabilistic) confidence interval that approximates the actual confidence interval being represented by the representation. These (estimated) confidence intervals can then be used in the detection of unknown-unknowns as previously described.

In some examples, the representation of the confidence interval is defined as a multi-variate Gaussian distribution. A multi-variate Gaussian distribution can be considered to be a plurality of Gaussian distributions, with each Gaussian distribution being defined by an average (e.g. a mean) and a standard deviation. The Gaussian distribution could also include a covariance matrix (which need not be used).

In some examples, the data processing apparatus comprises: error calculation circuitry to calculate an error between at least one of the future time series forecasters and the new measurement, wherein the confidence interval generation circuitry is configured to adjust the confidence interval of the at least one of the future time series forecasters of the aspect of the system based on the error. A process of refinement can be used for the confidence interval based on the new measurement. For instance, the new measurement can be compared to the forecaster to determine how close the measurement is to the forecaster. From there, the confidence interval can be adjusted (e.g. scaled) based on the proximity between the new measurement and a value predicted by the forecaster. A small proximity could result in the confidence interval size being reduced by a larger amount (e.g. by scaling or reduction) and a larger proximity could result in the confidence interval size being reduced by a smaller amount. The amended confidence interval can then be used for the detection of unknown-unknowns.

In some examples, the unknown-unknown detection circuitry is configured to determine that an unknown-unknown exists in response to a predetermined number of new measurements falling outside the confidence interval associated with each future time series forecaster of the aspect of the system. When the predetermined number (e.g. of a positive integer and/or a positive integer greater than one) of new measurements fall outside the confidence interval, it can be determined that an unknown-unknown exists. Such a scheme can be used to control the sensitivity of a system (e.g. whether the system is more sensitive, but also more susceptible to noise and vice-versa).

In some examples, the future time series forecaster of the aspect of the system and the confidence interval of the future time series forecast of the aspect of the system are provided as probability distributions generated based on historical measurements of the aspect of the system; the measurement circuitry is configured to generate a plurality of new measurements and a test distribution of the new measurements; and the unknown-unknown detection circuitry is configured to determine a distance between the test distribution and the probability distributions and in response to the distance between the test distribution and the probability distributions exceeding a threshold, to determine that the test probability distribution represents an unknown-unknown. In some of these examples, the probability distributions are generated using a variational autoencoder based on the historical data. For instance, the variational autoencoder could be a Long Term Short Memory (LTSM) variational autoencoder. In some examples, each class has a plurality of probability distributions generated, and a further probability distribution is generated, for each class, from those probability distributions. The distance can be calculated, for instance, using KL divergence.

Particular embodiments will now be described with reference to the figures.

FIG. 1 illustrates a data processing apparatus 100 in accordance with some embodiments. The data processing apparatus 100 can be used for generating confidence intervals and/or representations of confidence intervals that can be used in the detection of unknown-unknowns. The data processing apparatus includes storage circuitry 110 that is used for storing time series forecasters of an aspect of the system. The system can be thought of as a parameter of a system (e.g. an environment) for which predictions are made. For example, an aspect of a system could be a performance of a computer system (with the performance being the aspect and the computer system being the system). Another example of an aspect of a system could be a voltage of a heart (with the voltage being the aspect and the heart being the system) in the case of an echocardiogram. The forecasters deal with time series, which is to say that the aspect of the system for which a prediction is being made is dependent on the current state of the system; each change in the aspect of the system is not completely independent (it instead depends on the current value of that aspect of the system). There are lots of techniques that can be used to implement forecasters and the exact selection of technique is not relevant to the present technique. One example of a forecaster is a linear regressor, which can be thought as a mechanism used to produce a "line of best fit" across a series of data points. Confidence interval generation circuitry 130 is used to produce a confidence interval for each of the forecasters. A confidence interval makes it possible to not simply predict a value but to provide a range of values into which a future value may be expected to lie. The size of the confidence interval may depend on the level of confidence being expressed. Typically, as confidence increases, the confidence interval contracts and vice versa.

In classification problems, one is often concerned with categorising an item of data into one or more classes. Each class or category could therefore represent a different behaviour of the system. Consequently, the storage circuitry 110 may contain a number of different forecasters—one for each class. The forecast circuitry 120 can then produce a number of different forecasts. For instance, in the case where the aspect of the system is a performance of the computer system, one class could represent the computer system operating malware while another class could represent the computer system not operating malware. Indeed, a different class could be provided for each different type of malware or even each known malware product. In the case of heart monitoring using an echocardiogram, the classes could represent a patient with a normal heartbeat and a patient with arrhythmia. The forecast circuitry 120 could therefore provide forecasts of computer system performance/heartbeat voltage for each of the different classes for which a forecaster exists in the storage circuitry 110. Similarly, the confidence interval generation circuitry 130 can be used to generate a confidence interval for each of those forecasts. Note that the size of the confidence intervals might differ for each class. For instance, it may be more difficult to define a typical or normal heartbeat as opposed to a heartbeat of a patient with arrhythmia. Phrased differently, the number of possible representations for a "normal" heartbeat could differ far more than for a patient with arrhythmia. Consequently, the confidence interval for the class of "normal heartbeat" could be much wider than the confidence interval for the class of "patient with arrhythmia" even when the confidence intervals represent the same level of confidence.

The present technique recognises that an unknown-unknown could be defined as a data point that lies outside all of the confidence intervals generated by the confidence interval generation circuitry 130 for each of the classes. This is because such a data point falls outside what can be reasonably expected for each of the forecasts for each known class. This could occur, for instance, where the training set that has been used to generate the forecasters stored in the storage circuitry 110 is not sufficiently complete, where a training process used to generate the forecasters in the storage circuitry 110 have not been correctly formed, or where a new, previously unknown class existed. For example, taking the previous examples, and unknown-unknown may arise for a patient with a previously undiscovered variant of arrhythmia or for a patient having another heart condition for which the forecasters in the storage circuitry 110 were not prepared. In the case of a malware detector, an unknown-unknown could represent a previously unknown malware strain, a previously unknown type of malware, a new strain or type of benignware, or even a machine running software that is not strictly speaking malware, but shares many characteristics of malware such as spyware. Numerous actions can be taken in response to the detection of an unknown-unknown as will be discussed later.

There are a number of ways in which the unknown-unknown detection circuitry 140 can be used to detect unknown-unknowns. However, one use of this is the detection of unknown-unknowns in historical data (e.g. stored in the storage circuitry 110). This is particularly important in machine learning techniques where random samples of historical data may be used to train a forecaster. In these situations, if other historical training data that was not used to generate the forecaster is determined to be an unknown-unknown then this is indicative that the forecaster that has been generated is not acceptable and the training process must be re-performed.

Note that it is not necessary for the raw confidence intervals to be used by the unknown-unknown detection circuitry 140. Although these can be used, they may be large requiring a large amount of storage space to be used properly. Consequently, in some embodiments of the present technique, simplified representations of the confidence intervals are used. These can be generated, for instance, by the estimated confidence interval generation circuitry, using the confidence intervals themselves. A technique for this will be illustrated below.

Figure 2:
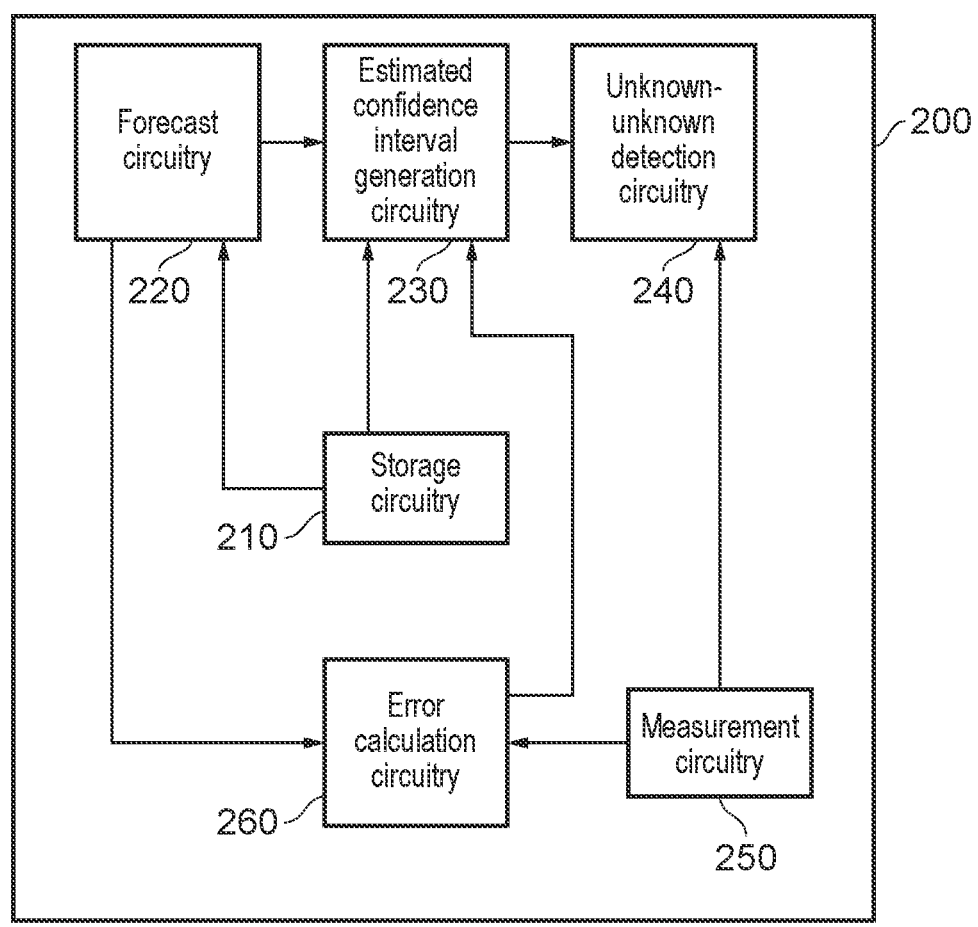
FIG. 2 illustrates a data processing apparatus in accordance with some embodiments.

Furthermore, having generated a simplified representation of the confidence interval, the simplified representation can then be used (e.g. in a separate data processing apparatus 200) without the need for the original confidence interval. FIG. 2 illustrates such an apparatus. In this apparatus, the storage circuitry 210 stores forecasters as for FIG. 1. The forecasters are used by the forecast circuitry 222 to generate forecasts. Estimated confidence interval generation circuitry 230 uses the representation of the confidence intervals (provided for each of the forecasters) to generate a confidence interval for each forecast. Measurement circuitry 250 can be used in order to generate new measurements. The measurement circuitry could, for instance, comprise a sensor for sensing the aspect of the system for which the forecaster present. Unknown-unknown detection circuitry 240 is then used to detect an unknown-unknown as a measured point that falls outside each of the confidence intervals. In addition, error calculation circuitry 260 can be used in order to determine an error between the measured value obtained by the measurement circuitry 250 and a value from the forecast produced by the forecast circuitry 220. This difference can then be used by the estimated confidence interval generation circuitry 230 in order to adjust the confidence intervals that are generated. For instance, if the measurement produced from the measurement circuitry 250 happens to lie exactly on the forecast, then the confidence intervals may be left alone. If the measurement produced from the measurement circuitry 250 lies at one extreme of the confidence intervals, then the confidence intervals may be moved (e.g. by scaling or by addition) such that the measurement value lies more centrally within the confidence interval. The extent to which the confidence intervals are moved may be dependent on the difference between the measured value and the forecast. In some examples, the movement of the confidence intervals in this manner may be dependent on not just one measurement and the forecast but a series of measurements and the forecast. For instance, it may be determined whether the measurement produced by the measurement circuitry 250 are generally different from the forecasts produced by the forecast circuitry 220.

Some of the above described processes will now be shown in more detail.

Figure 3:
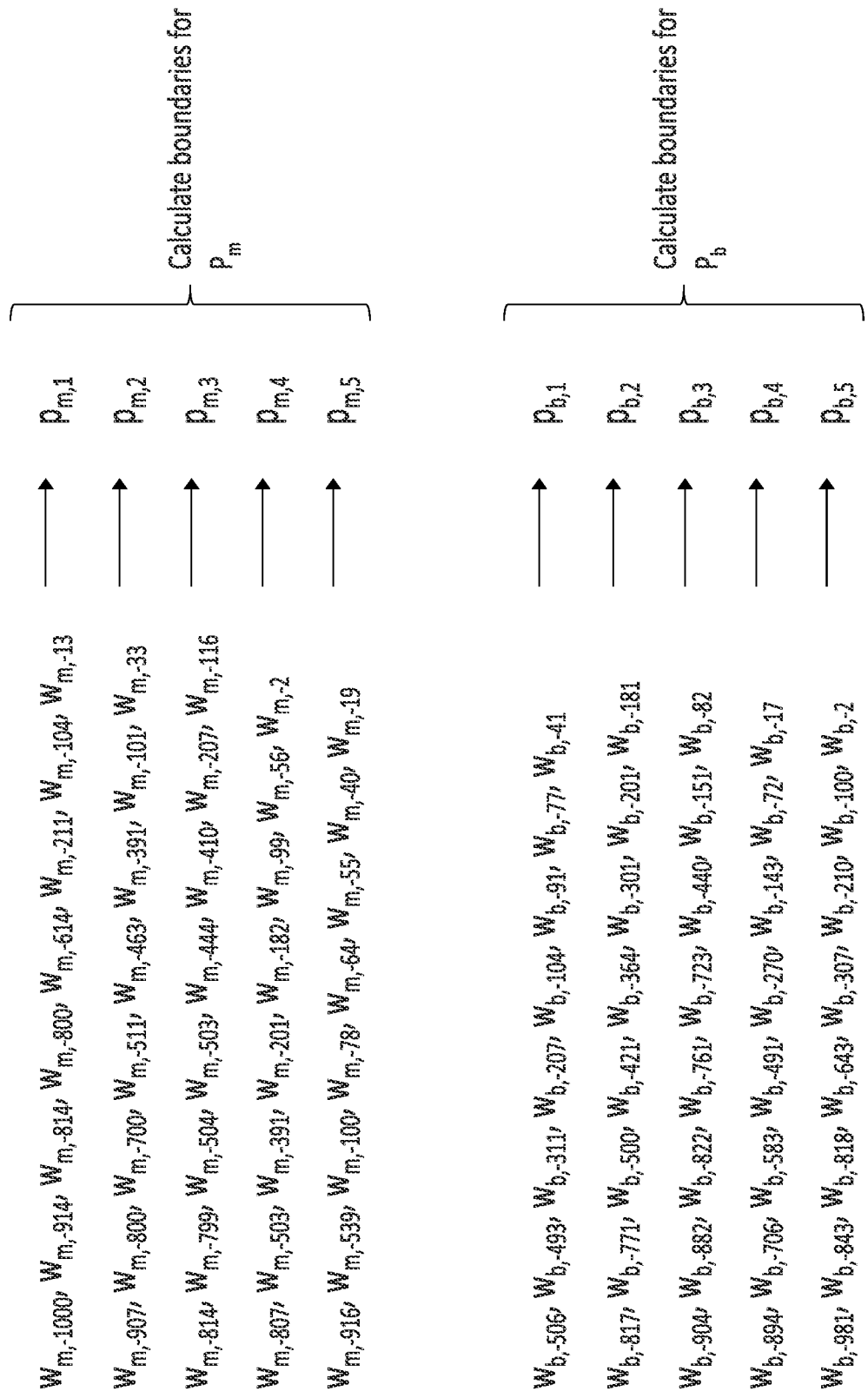
FIG. 3 illustrates a process of "bootstrapping" that can be used for the generation of a forecast.

FIG. 3 illustrates a process of "bootstrapping" that can be used for the generation of a forecast. Here, it is assumed that there are two classes—benignware (b) and with malware (m). For each of the two classes, 1000 windows of historical data are present, each window representing a number of contiguous data points in a time series that expresses the performance of the system operating with benignware (e.g. without malware) or with malware. Each forecast is produced by randomly selecting eight such windows and combining these windows one after another in order to produce a sliding-window forecast that extends over the next eight windows. For instance, a first forecast $P_{m,1}$ of a system operating with malware is produced by plotting a line in which a first window is represented by the window at historic window $w_{m,-1000}$, the forecast then continues in the same manner as it does for the historic window $w_{m,-914}$, and then for the window $w_{m,-814}$, and then for the window $w_{m,-800}$, and then for the window $w_{m,-614}$, and then for the window $w_{m,-211}$, and then for the window $w_{m,-104}$, and then for the window $w_{m,-13}$. So for example, if the window $w_{m,-1000}$ were to start at a performance value of 40 then so too would this particular forecast. If the window $w_{m,-1000}$ were (over its data points) to cause a decrease of performance by 5%, then so too would the first window for this forecast, resulting in a final performance value of 35% (40−5). If the window $w_{m,-914}$ were to illustrate an increase in performance by 7% over its data points then the next window of the forecast would increase to 42% (35+7) by the end. If the window $w_{m,-814}$ were to have no overall change (e.g. perhaps the data points rise and then fall back down to the original level) then by the end of the third window of the forecast, the performance value would remain at 42%. This process continues until all of the historic windows have been applied and an overall forecast has been produced. FIG. 3 illustrates five forecasts being produced for each of the two classes. In each case, the historic values taken to reduce the forecast are of the same class for which the forecast is being generated. That is, a forecast for the behaviour of a system operating with malware uses historic data also corresponding to a system operating with malware and does not use historic data corresponding to a system without malware (e.g. with benignware). It will be appreciated that the number of windows used to generate each forecast can vary depending on the implementation although generally will be the same for each of the forecasts that have been generated. Similarly, the number of historic windows that are used will also depend on the implementation. FIG. 3 shows an example of uncorrelated bootstrapping for time series. However, the present technique is equally applicable to other forms of bootstrapping such as smoothed correlated bootstrapping or naïve bootstrapping.

Figure 4:
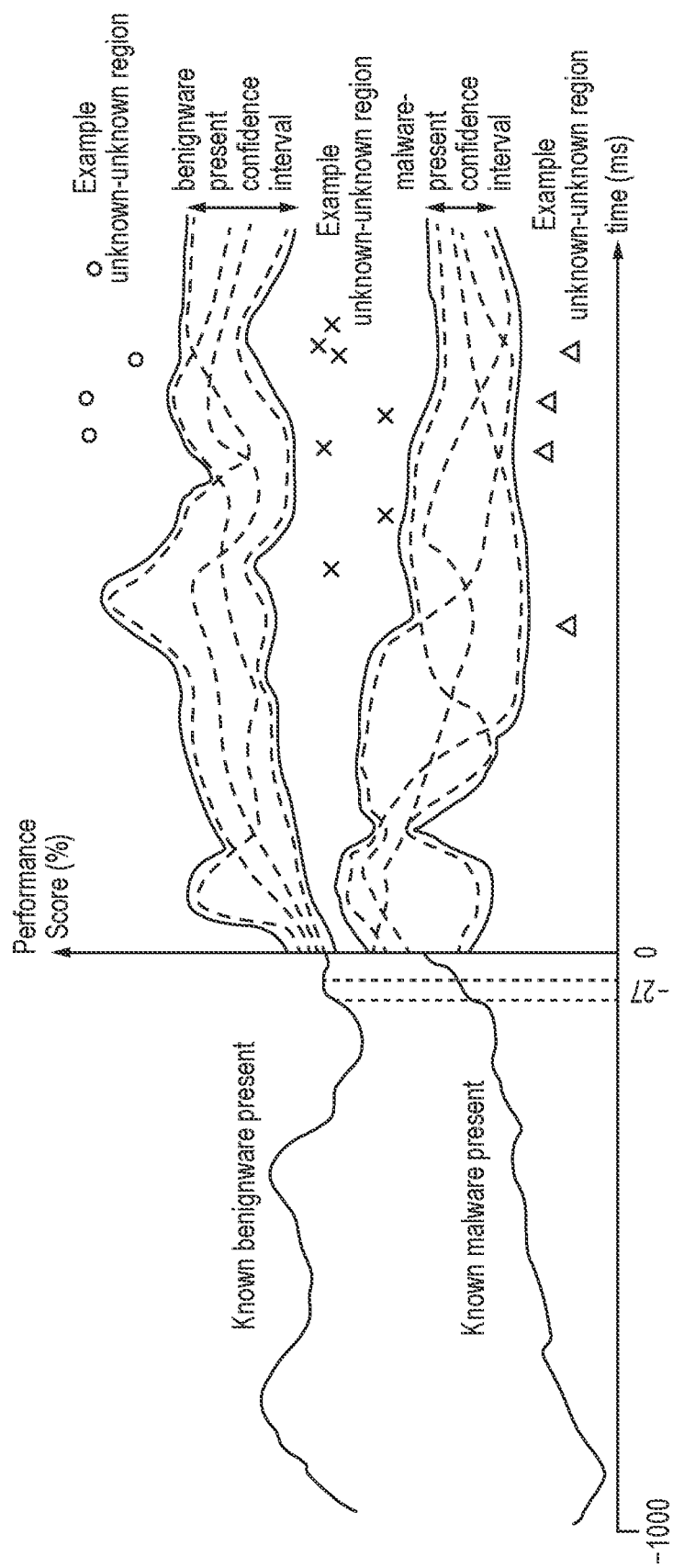
FIG. 4 illustrates the generation of the confidence intervals for each of the classes.

FIG. 4 illustrates the generation of the confidence intervals for each of the classes. In particular, the confidence intervals are generated based on a maximum point across each of the forecasts of a class for each time. One way of achieving this is simply for the confidence interval at each point in time to be the maximum value of each of the forecasts of a class at that time. In other examples, the confidence interval could be defined as a point that encompasses some percentage of each of the forecasts at that time. For instance, the confidence interval could be defined such that it covers 95% of the likely forecasts (i.e. the $95^{th}$ percentile). In other examples, the confidence interval could be defined as being a percentage of the value at each time across each of the forecasts. Other techniques will be known to the skilled person. FIG. 4 therefore illustrates how historic data (represented from a window at a time period −1000 to a window at a time period 0) of the two classes in a malware detector can be used to produce four different forecasts for each of the two classes. Confidence intervals are then generated based on the forecasts for each class. An unknown-unknown can then be considered to be any data point that lies outside all of those confidence intervals, and FIG. 4 shows example unknown-unknown regions (e.g. between the confidence intervals).

Note that in some examples some leeway may be given for the detection of an unknown-unknown. For instance, an unknown unknown may be required to be a certain distance away from each of the confidence intervals.

Figure 5:
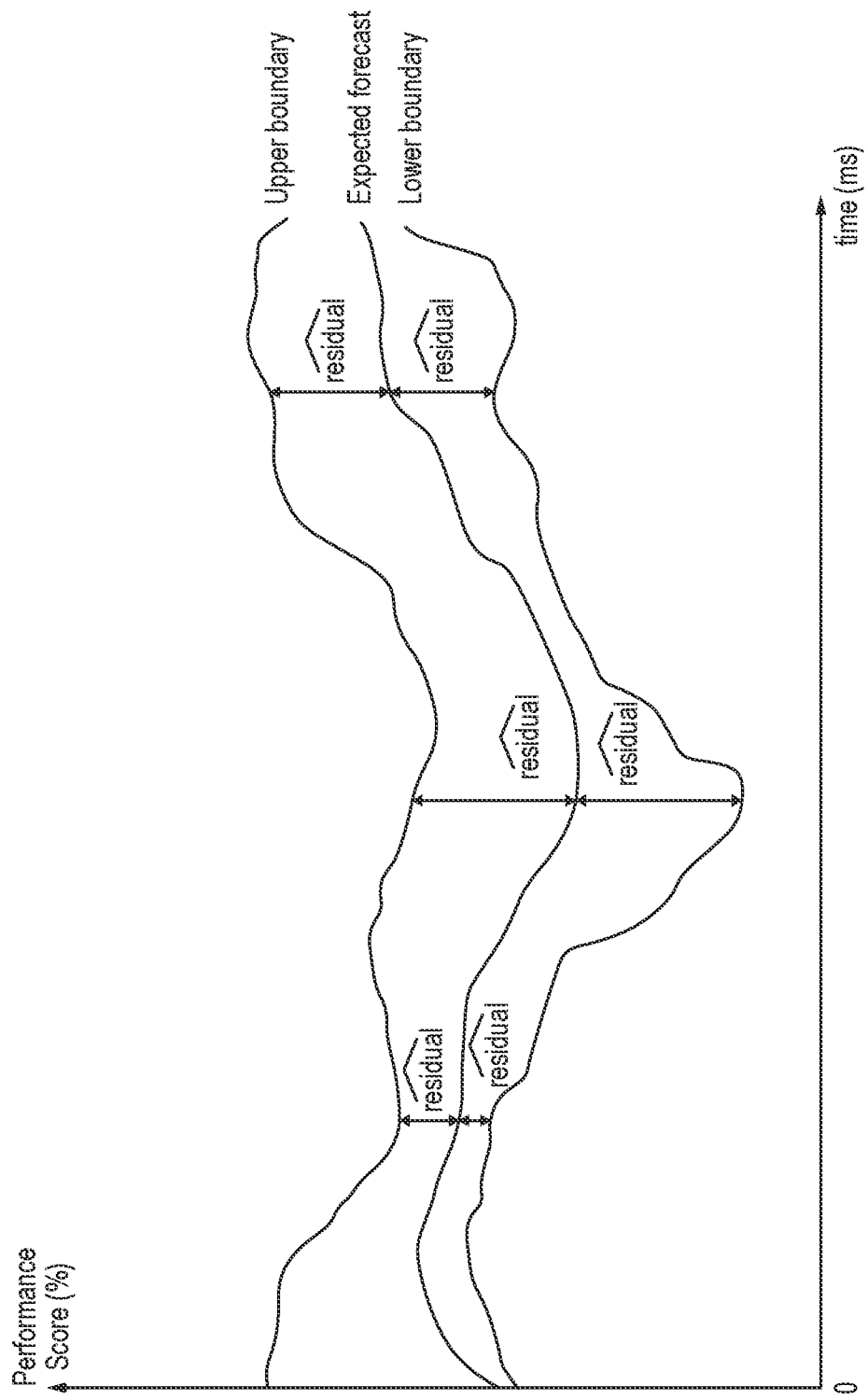
FIG. 5 illustrates an expected forecast.

In practice, computing and storing the raw confidence intervals is expensive. An alternative to this is to store and use a simplified representation of a confidence interval that approximates the confidence interval. This can be generated based on the confidence interval itself. One way of generating this is based on residuals (which might be sampled). A residual can be considered to be the difference between the confidence interval and a value that is accepted as being a 'ground truth'. For instance, FIG. 5 illustrates an example in which an expected forecast is used as a 'ground truth'. The expected forecast can be generated by determining, at each time, the average value across each of the forecasts that were generated for a single class (e.g. as illustrated by the dashed lines in FIG. 4). The residual at each time then corresponds with the difference between the expected forecast and the upper/lower boundary. Having determined the residuals, a simplified representation of the confidence interval can then be determined by looking at the average (e.g. mean) and standard deviation of the residuals across the time series. In many cases, the distribution of residuals will follow a Gaussian distribution. The confidence intervals for each forecast can therefore be represented as a multi-variant Gaussian distribution (e.g. one Gaussian distribution for the residuals of each class). This details of a Gaussian distribution can be stored in a significantly smaller amount of storage space than the raw values themselves.

The following code is an example of a simple program for generating a set of statistics that represent a confidence interval in a simplified manner:

```
def get_independent_bootstrap_distributions(residuals, n=1000, m=5O):
# Assume residual in N^r, where r is number of channels in time series
mus = np.array((n, residual.shape)) # n x r
std = np.array((n, residual.shape)) # n x r
for i in range(n): #Do n times
R = select m random samples from residuals # Each row is a sample
# R is R^{mxr}
mus[i][:] = np.mean(R, axis=0) # Compute mean across samples
std[i][:] = np.std(R, axis=0) # Compute stddev across samples
# Store the stats for the stats
mus_mu = np.mean(mus, axis=0)
mus_std = np.std(mus, axis=0)
std_mu = np.mean(std, axis=0)
std_std = np.std(std, axis=0)
return mus_mu, mus_std, std_mu, std_std
#Store mus_mu, mus_std, std_mu, std_std
horizon_stats = [ ]
for i in range(num_horizons):
horizon_stats.append(get_independent_bootstrap_distributions{horizon_residuals[i], n, m))
```

The resulting data can be used as the representation of a confidence interval in either the data processing apparatus 100 illustrated in FIG. 1 or in the data processing apparatus 200 illustrated in FIG. 2. Each a similar process can be used for generating the overall forecast.

A different data processing apparatus can generate an estimated confidence interval from the representation of a confidence interval and a forecast (either from a forecaster or from a simplified representation of a forecaster) and then applying errors to the forecast by using samples from the representation of the confidence interval. For instance, given an average and a standard deviation, it is possible to produce a representative value from that distribution. This sample can then be used as the next residual for the forecast. A plurality of samples is used to produce the upper and lower boundaries of the estimated confidence interval for the forecast. Consequently, as estimated confidence interval is produced from a representation of an actual confidence interval, with the estimated confidence interval corresponding statistically with the actual confidence interval, without all of the data of the confidence interval being required. As previously shown, these estimated confidence intervals can then be used in the identification of unknown-unknowns.

Following on from the above code example, the sampling can be performed as follows:

```
def sample_residual_from_stats{mus_mu, mus_std, std_mu, std_std):
mu = np.random.normal(mus_mu, mus_std) #return vector of sampled mu in N^r
```

```
std = np.random.normal(std_mu, std_std) #return vector of sampled
std in N^r
sample = np.random.normal(mu, std) # Return a sample in N^r
return sample
```

Figure 6:
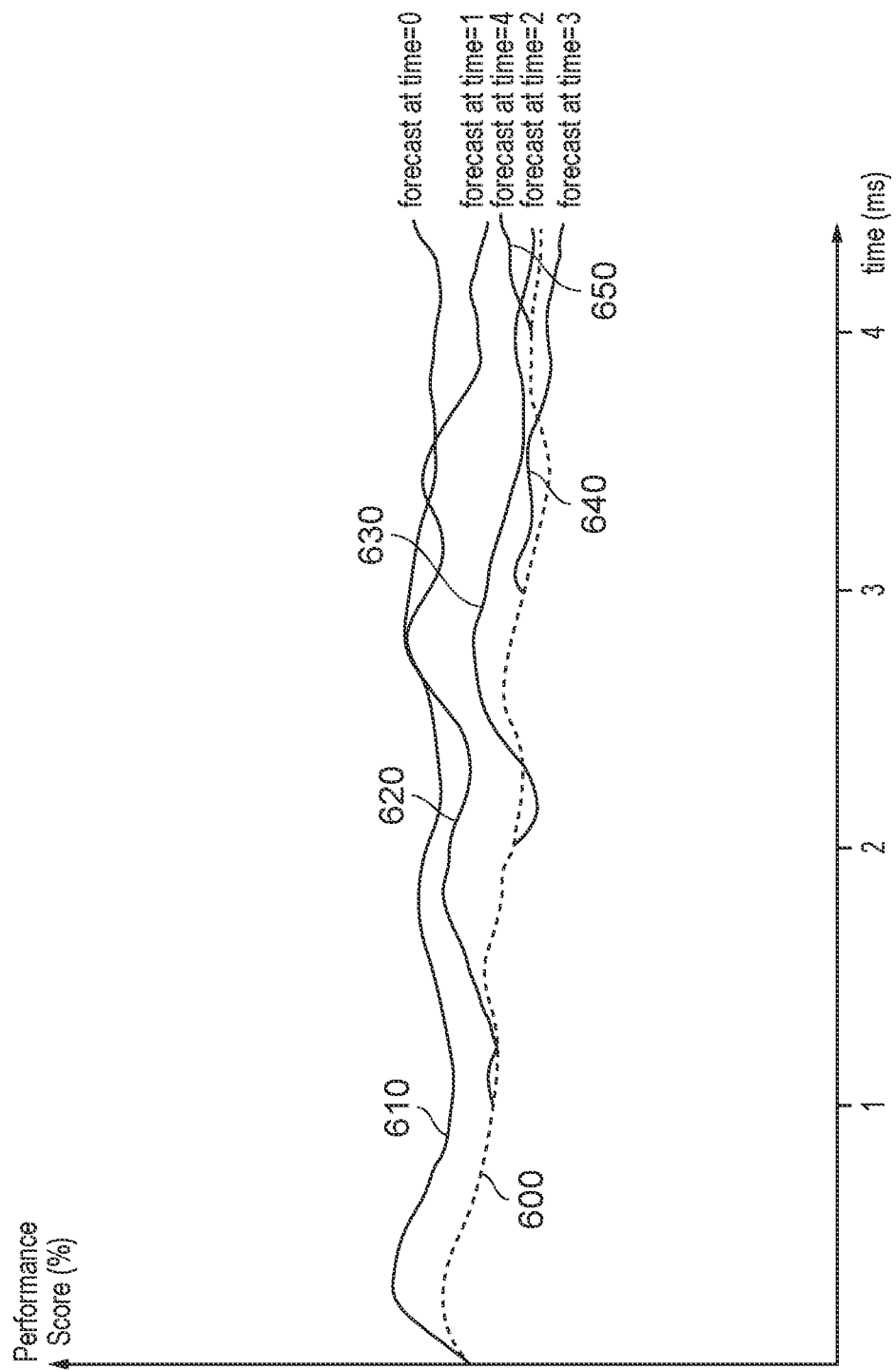
FIG. 6 illustrates a way in which the confidence intervals (e.g. estimated confidence intervals) can be adjusted based on new measurements.

FIG. 6 illustrates how actual measurements can be used in order to improve the generation of the confidence intervals, and thereby improve the detection of unknown-unknowns. In the example of FIG. 6, actual measurements are made (shown by dashed line 600). At each time period, the actual measurements gathered so far (together with any historical data and/or forecasters available to the system) are used to generate a new future prediction. These future predictions are able to consider the residuals—specifically the difference between the previous future forecast that was made and the actual measurements taken. Consequently, as time goes on, each forecast is made with the new forecasts incorporating the latest measurements.

Initially, a first forecast 610 is made. At a time t=1, the system is able to compare that forecast 610 with the measurements 600 that have been taken up until that point. It will be noted that in this example, the actual measurements are close, but generally fall below the prediction). A new forecast 620 is generated. This forecast is able to take the more recent measurements into account. Indeed, it will be noted that (at least initially), the measurements then track much more closely with the latest prediction 620. At a time t=3, the residual is larger and a new prediction 630 is made based on the historic measurements that are now available (from t=0 to t=2). Similarly at time t=3 another new prediction 640 is made and at a time t=4 a still further new prediction 650 is made. Each time a new prediction is made, it is made on the basis of additional new measurements that were not available when the previous predictions were made.

In terms of confidence intervals, one can consider the boundaries of all the forecasts that are generated over time. However, as time goes on, each forecast is made with increased historical knowledge. One might therefore expect the forecasts to change their accuracy as time goes on. Consequently, by considering a percentile that the forecasts fall into, the less accurate forecasts can be excluded. One technique is therefore to consider the residuals (the difference between the measurements and the forecast for a window) and to consider the confidence intervals as encompassing those forecasts where the residual lies within the 95$^{th}$ percentile. As before, an unknown-unknown can be identified by falling outside the confidence intervals.

Note that this technique is agnostic to the technique used to produce the forecasts. In some examples, the forecasts could use the previously described bootstrapping technique in which random samples are taken from the representation of the confidence interval, and these are used to extent a 'current' measurement. In other examples, a regular forecaster such as a regression forecaster might be used. In any case, by placing the confidence intervals at a given percentile, the system is able to adjust and weed out outlying forecasts.

The calculation of a percentile range typically requires an ordering of elements. Without this, when new elements (e.g. forecasts/residuals) are added, it becomes impossible to know where a particular percentile lies (in a similar way that determining the median value in a set of values generally necessitates each of those values to be known). This is resource intensive. One technique that can be used to reduce the resource consumption is min-sketch, also known as count min-sketch, which allows functions such as median or percentiles to be approximated with fixed memory requirements and predictable error rates.

An alternative to the bootstrapping process illustrated with respect to FIGS. 3 and 4 is to use a variational autoencoder such as a Long Short Term Memory LSTM) variational autoencoder in order to produce distributions representing the latent space, learned compressed encodings, of classes of historical time series (in effect, an overall distribution of those distributions can be generated).

This overall (class) distribution can then be compared to distributions of new measurements projected into the latent space of each class. An unknown-unknown is said to occur where the measured distributions are sufficiently different from each corresponding (class) distribution. LSTM variational autoencoders can be considered as a class of neural network containing feedback loops. These can be trained by using the historical time series for a class as training data and produce an expected distribution of the data for that class. The variational autoencoder may provide a distribution for each window. The distributions for all of the windows of a class can then be combined in order to produce an overall distribution for that class. This technique is demonstrated in the following figures.

Figure 7:
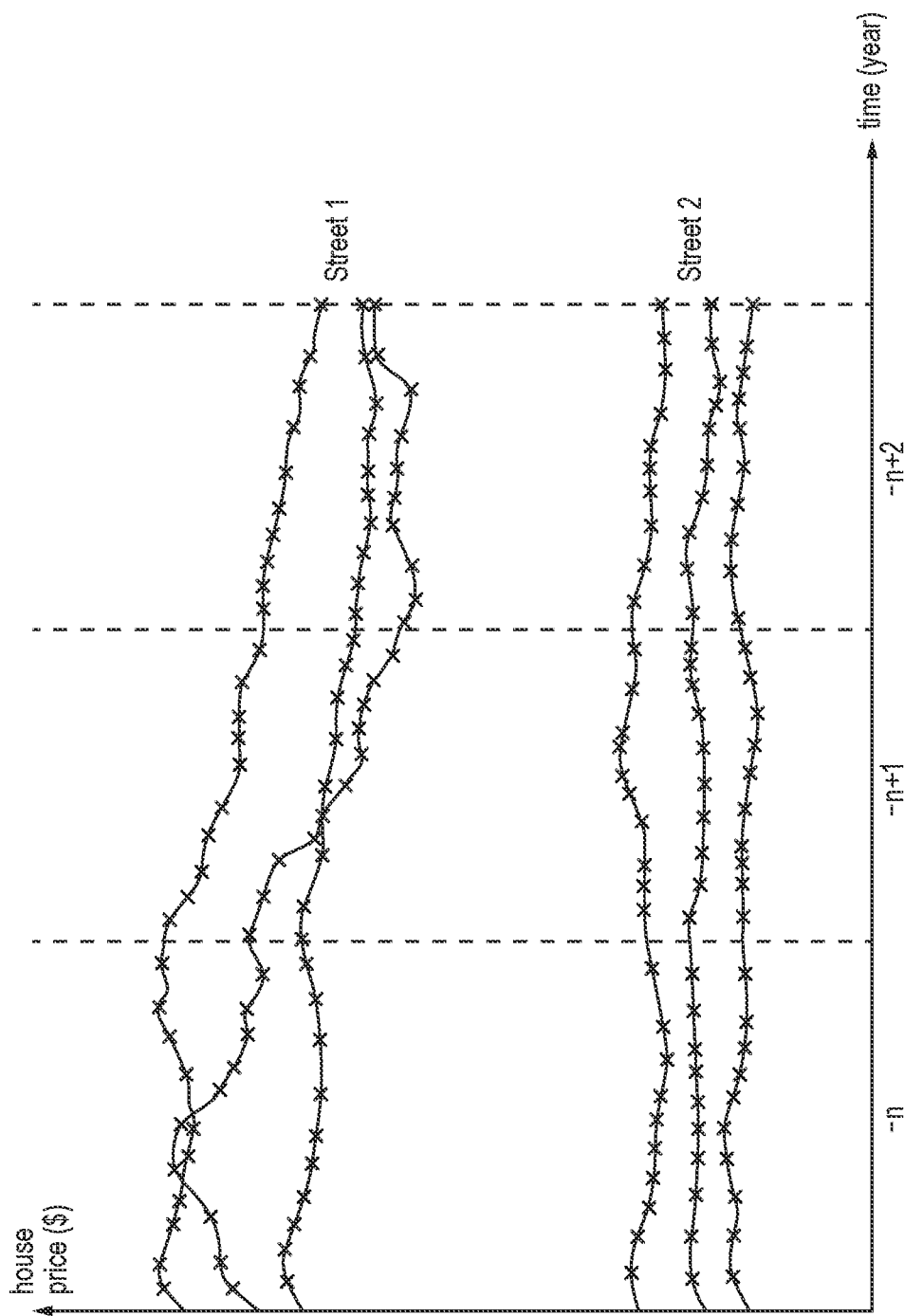
FIG. 7 illustrates sets of historical measurements used to produce six time series.

FIG. 7 illustrates sets of historical measurements used to produce six time series. In this example, each measurement is the value of a given house in a particular street (street 1 or street 2) and so each time series shows the value of a house over time. The concept of a house price has been chosen here purely for variety and exactly the same technique can be applied to other previously mentioned examples (such an echocardiograms or computer system performance). This historical data therefore illustrates the house price of six different houses in each of two streets. An LSTM variational autoencoder can be applied to each class (the streets) in order to produce a distribution of house prices for each class for each year.

Before going further, it is important to recall that the goal here is not to predict a house price. This example would be concerned with the idea of identifying a street that a house was located in, based on the change in price of that house over time and in particular, we are concerned with the idea of detecting unknown-unknowns—which in this example could include both house price trends for houses in other streets or house price trends of houses that are in street 1 or street 2 that would appear to be 'abnormal' based on the house price trends that are in this training data.

An LSTM autoencoder can be applied to each of the time series of each window for each class. So, for instance, the LTSM autoencoder would firstly be applied to the top three trend lines in the window '−n' to produce a first distribution for the class (street 1). The LTSM autoencoder can then be applied to the top three trend lines in the window '−n+1' to produce a second distribution for the class, and then to the window '−n+2' to produce a third distribution for the class. The process can then be repeated for the same three windows of the second class (street 2).

As previously explained, the present techniques are not limited to any particular form of training data or problem based on categorisation. Other examples could include the collision avoidance detection through the detection of people in automated vehicle systems (e.g. versus photographs of people), the detection of falls (based on walking behaviour) in vulnerable people, and so on.

Figure 8:
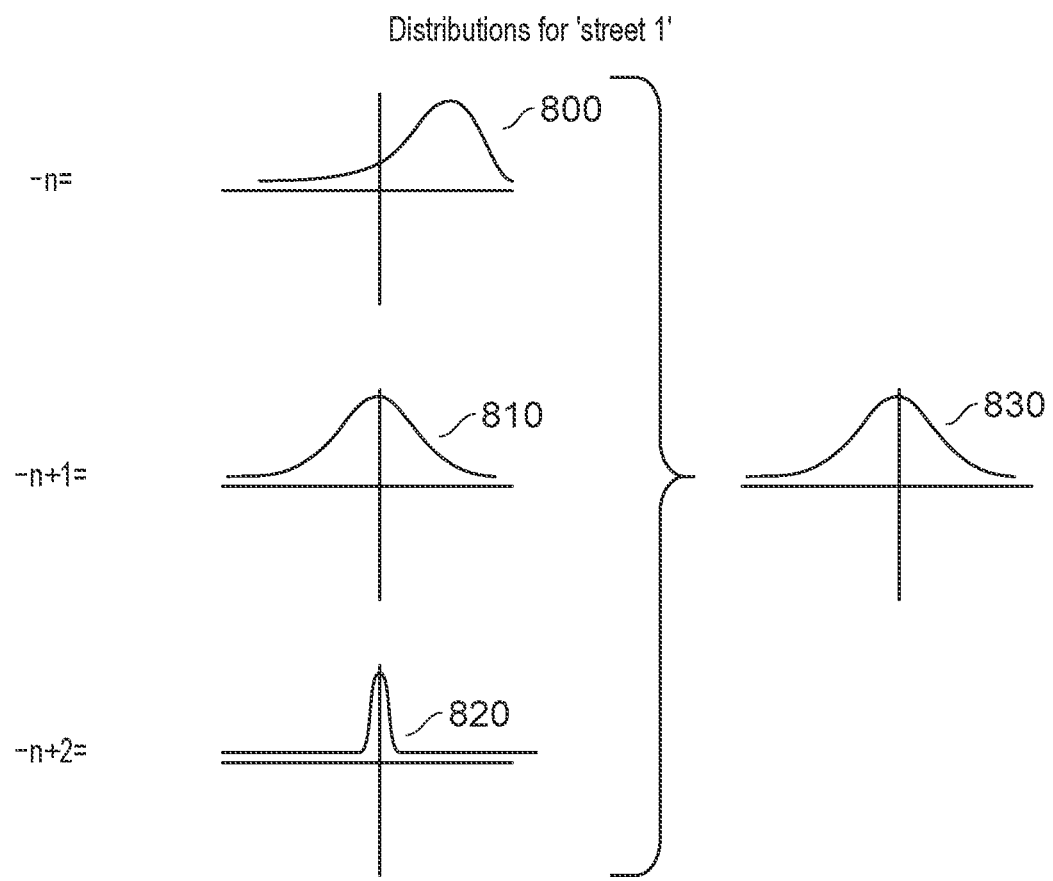
FIG. 8 illustrates example distributions that may be achieved for each of the windows in FIG. 7.

FIG. 8 illustrates example distributions 800, 810, 820 that are achieved for each window (−n, −n+1, −n+2) for the class 'street 1'. These three distributions can be combined as part of a machine learning process in order to produce an overall distribution 830.

Figure 9:
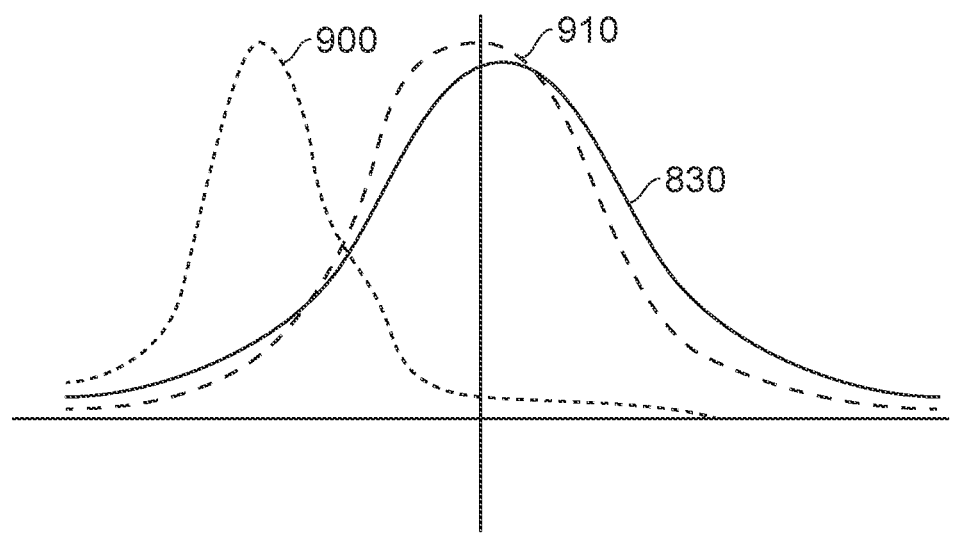
FIG. 9 shows relationships between distributions.

The overall distributions can be used as a representation of the hypothesis test against the confidence interval in exactly the manner described above with reference to FIGS. 4-7. However, another option is to use a corresponding variational autoencoder (the decode stage of the variational autoencoder isn't needed at inference time, since it is knowledge of the latent space that is required to compare the two distributions) to produce a distribution of new measurements that are made within a window of time. This is illustrated in FIG. 9. In particular, the distribution of a set of measurements over a window is compared to the overall distribution 830 that was previously calculated. If the two distributions closely correspond, then the measurements can be said to belong to the class for which the overall distribution 830 was generated. If the two distributions differ, then the measurements are unlikely to belong to the class for which the overall distribution 830 was generated. If one overall distribution 830 is generated for each class and if the distribution of measurements is sufficiently different from each of the generated overall distributions 830, then the measurements correspond to an unknown-unknown.

In the example of FIG. 9, the distribution 900 of a first set of values differs greatly from the overall distribution 830 that was generated for the class and therefore the distribution does not belong to the class. If this is the only class, then this distribution 900 is likely to be an unknown-unknown. In contrast, a second distribution 910 of a second set of values closely resembles the overall distribution 830 that was generated for the class and therefore the distribution is likely to belong to the class. There are a number of ways of determining the similarly. However, some examples use KL divergence, which considers how much one distribution has to be changed in order to make it match the other distribution.

Figure 10:
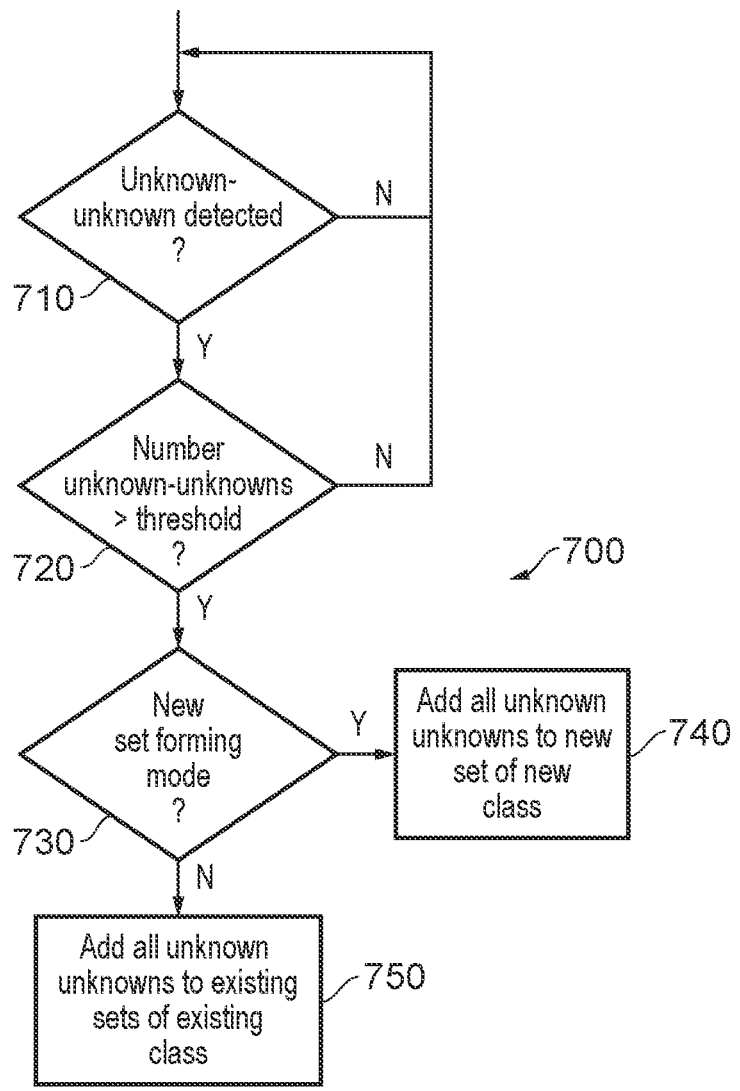
FIG. 10 illustrates a way in which the confidence intervals (e.g. estimated confidence intervals) can be adjusted based on new measurements.

There are a number of possibilities regarding how the detection of an unknown-unknown can be dealt with. FIG. 10 illustrates a flowchart 700 that shows process for deciding how such a data point should be handled. At step 710, it is determined whether an unknown-unknown has been detected. If not, then the process loops round to step 710. Consequently, the process waits until an unknown-unknown has been detected. Once an unknown-unknown has been detected, step 720 asks whether the number of unknown-unknowns that have been detected is greater than a threshold value. The threshold value is an integer greater than zero and can, in some examples, be equal to one. If not, then the process returns to step 710 to wait for another unknown-unknown to be detected. If the number of detected unknown-unknowns is greater than the threshold, then at step 730, it is determined whether a new-set-forming mode is enabled. In this mode, the system is designed to have a tendency to use unknown-unknowns to generate a new set of training data that can be used in the detection of a new class. Consequently, if such a mode is enabled, then at step 740, all of the unknown-unknowns are added to a new set of training data that represents the new class. Otherwise, at step 750, all of the unknown-unknowns are added to existing sets that correspond with existing classes. In practice, steps 730, 740, and 750 may require human intervention. In particular, it may be necessary for a human to analyse the unknown-unknowns in order to determine whether they should form the basis of a new set/class or whether they should be added to existing classes. In addition, human intervention may be necessary in order to determine which class each unknown unknown is to be added to. Of course, it is possible for other automated techniques to be used. For instance, one technique that could be used is for any unknown-unknown within a particular distance of an existing class to be added as a data point for that class will stop in other situations where the unknown-unknown is some distance away from each of the classes, the unknown unknown is used to form the basis of a new class.

Figure 11:
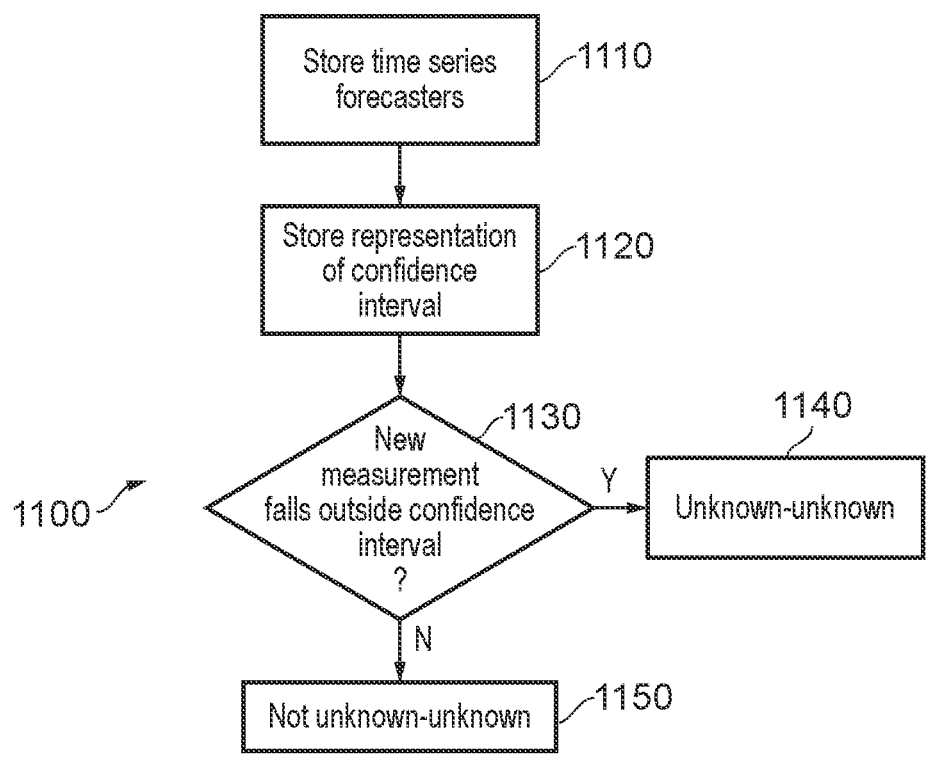
FIG. 11 is a flowchart that shows a method of data processing.

FIG. 11 illustrates a flowchart 1100 that represents a method of data processing in accordance with some examples. At a step 1110, a time series forecaster is stored. At a step 1120, a representation of a confidence interval is stored. At a step 1130, it is determined whether a new measurement falls within the scope of the confidence interval or not. If so, then at step 1140 that new measurement is labelled as an unknown-unknown. Otherwise at step 1150, the new measurement is not labelled as an unknown-unknown.

Concepts described herein may be embodied in computer-readable code for fabrication of an apparatus that embodies the described concepts. For example, the computer-readable code can be used at one or more stages of a semiconductor design and fabrication process, including an electronic design automation (EDA) stage, to fabricate an integrated circuit comprising the apparatus embodying the concepts. The above computer-readable code may additionally or alternatively enable the definition, modelling, simulation, verification and/or testing of an apparatus embodying the concepts described herein.

For example, the computer-readable code for fabrication of an apparatus embodying the concepts described herein can be embodied in code defining a hardware description language (HDL) representation of the concepts. For example, the code may define a register-transfer-level (RTL) abstraction of one or more logic circuits for defining an apparatus embodying the concepts. The code may be define a HDL representation of the one or more logic circuits embodying the apparatus in Verilog, SystemVerilog, Chisel, or VHDL (Very High-Speed Integrated Circuit Hardware Description Language) as well as intermediate representations such as FIRRTL. Computer-readable code may provide definitions embodying the concept using system-level modelling languages such as SystemC and SystemVerilog or other behavioural representations of the concepts that can be interpreted by a computer to enable simulation, functional and/or formal verification, and testing of the concepts.

Additionally or alternatively, the computer-readable code may embody computer-readable representations of one or more netlists. The one or more netlists may be generated by applying one or more logic synthesis processes to an RTL representation. Alternatively or additionally, the one or more logic synthesis processes can generate from the computer-readable code a bitstream to be loaded into a field programmable gate array (FPGA) to configure the FPGA to embody the described concepts. The FPGA may be deployed for the purposes of verification and test of the concepts prior to fabrication in an integrated circuit or the FPGA may be deployed in a product directly.

The computer-readable code may comprise a mix of code representations for fabrication of an apparatus, for example including a mix of one or more of an RTL representation, a netlist representation, or another computer-readable definition to be used in a semiconductor design and fabrication process to fabricate an apparatus embodying the invention. Alternatively or additionally, the concept may be defined in a combination of a computer-readable definition to be used in a semiconductor design and fabrication process to fabricate an apparatus and computer-readable code defining instructions which are to be executed by the defined apparatus once fabricated.

Such computer-readable code can be disposed in any known transitory computer-readable medium (such as wired or wireless transmission of code over a network) or non-transitory computer-readable medium such as semiconductor, magnetic disk, or optical disc. An integrated circuit fabricated using the computer-readable code may comprise components such as one or more of a central processing unit, graphics processing unit, neural processing unit, digital signal processor or other components that individually or collectively embody the concept.

In the above description, it has been explained that an element of refinement of a forecast or confidence interval can be performed by the use of new measurements. One way in which this can be achieved is described below. However, it will be appreciated that the techniques below could also be used in isolation.

Figure 12:
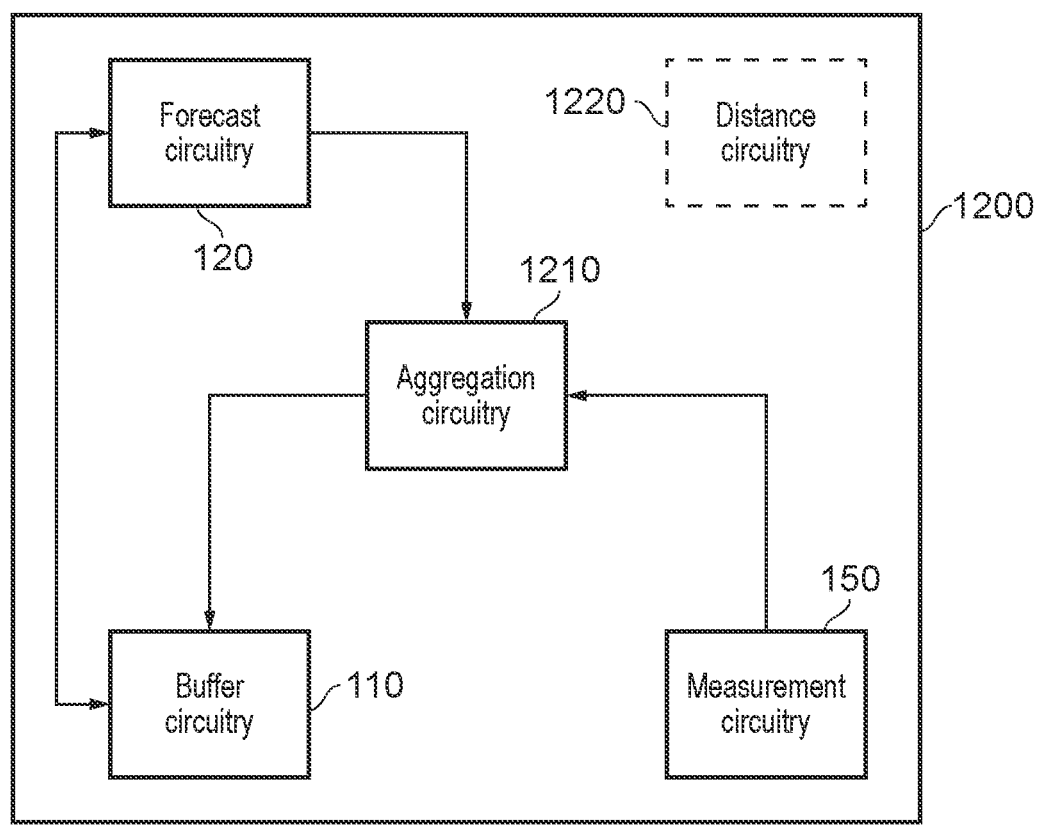
FIG. 12 illustrates a data processing apparatus in accordance with some embodiments.

FIG. 12 illustrates a data processing apparatus 1200. This might be the same data processing apparatus 100 illustrated in FIG. 1 or the same data processing apparatus 200 illustrated in FIG. 2 or could be altogether different. In any event, the data processing apparatus 1200 includes forecast circuitry 120, similar to that already described, and suitable for producing a forecast of an aspect of a system (e.g. using a linear regressor). Measurement circuitry 150 is also provided for obtaining a new measurement. This new measurement could be produced from, e.g. a sensor or other device capable of measuring the aspect of the system. Alternatively, the new measurement could simply be an item of data that has not been used in the training of the forecasters used in the forecast circuitry 120. Aggregation circuitry 1210 is used to aggregate the new measurement for a period or window or time together with the forecast previously produced for that period or window of time. The resulting aggregation is then used by the forecast circuitry 120 in order to revise later forecasts using the aggregation. A buffer 110 is provided to store the forecasts and aggregations.

It will be appreciated that since forecasts are revised using an aggregation of current measurement and previous forecast, that the forecasts will be adjusted based on new measurements. In this way, the relationship between the new measurement and the corresponding forecast can be taken into account when preparing new forecasts for later windows or periods.

The example of FIG. 12 also includes distance circuitry 1220, whose purpose will be described in more detail below.

FIG. 13 shows an example of the aggregation process. At a time t0, an initial set of predictions are made for windows $w_1$, $w_2$, and $w_3$ (e.g. that begin at time $t_1$, $t_4$, $t_7$). Each window is made up of three measurements/data points.

Starting at a time $t_1$, measurements can be made across the first window $w_1$ (i.e. at times $t_1$, $t_2$, $t_3$). These measurements can then be aggregated with the previous forecast for window $w_1$. In this case, the aggregation is a simple averaging, which is carried out for each (forecast, measurement) pair for the window. The resulting aggregation ([6.5, 15, 6.5]) can then be used as a basis for producing future forecasts using the existing forecasters. This then results in a revised prediction for $w_2$ and $w_3$. Note that this can be achieved in a circular buffer which, in this case, is able to store data for three windows. Since the data for $w_1$ will then no longer be needed, it can be used to produce a prediction for a new window $w_4$ before being replaced by that prediction. It will be appreciated that this technique can be performed cyclically. In particular, at the next window $w_2$, a new set of measurements can be produced, and these can be aggregated with the revised prediction for $w_2$. The resulting aggregation can then be used to produce a still further revised prediction for $w_3$, a revised prediction for $w_4$ and a new prediction for $w_5$. As time goes on, each prediction becomes revised more and more based on new measurements, and later predictions become increasingly refined and biased towards the new measurements that are taking place. In this way, the initial forecasts are tuned based on new measurements that are received.

FIG. 14 shows a variant in which a different weighting is used between the previous forecast for a window and the actual measurements taking place. Whereas, in FIG. 13, the forecast and new measurement were weighted equally, in FIG. 14, the two numbers are weighted more in favour of the new measurement rather than the forecast (by a ratio of 3:1). Consequently, the revised forecast that is produced will lean more strongly towards the new measurements rather than towards the forecasts.

Confidence interval generation can take place using any of the previously described techniques. For instance, the confidence intervals might be generated so as to encapsulate 95% of the residuals between the (revised non-aggregated) forecasts and the measurements.

One way in which this fine-tuning process can be used is to improve upon generically trained data in favour of a more specific system. For instance, considering the situation of malware detection, an extensive amount of training might take place on CPUs belonging to a number of different manufacturers. This training might then be considered to be relatively good in terms of detecting malware on CPUs from (virtually) any manufacturer. Yet, the predictions produced by a forecaster trained in this way can be made even more accurate by looking at how measurements tend to differ from reality for a specific CPU. That is, although the overall predictions might be good, it might be discovered that when implemented in respect of a CPU from manufacturer X, the predictions are 4% too high, and when implemented in respect of a CPU from manufacturer Y, the predictions are 2% too low. With this knowledge, the predictions can be fine-tuned to better represent the specific system for which the forecast is being made. Similarly, in respect of, ECG analysis. It might be determined that the lifestyles or diets of the average person in one country require a slight deviation for a forecast produced from training a generic data set (or even from a biased data set such as where data was collected for people from a single country). Actual measurements, and specifically, consideration of the relationship between the actual measurements and the corresponding predictions can therefore be used to adjust the predictions for 'local considerations'.

Figure 15:
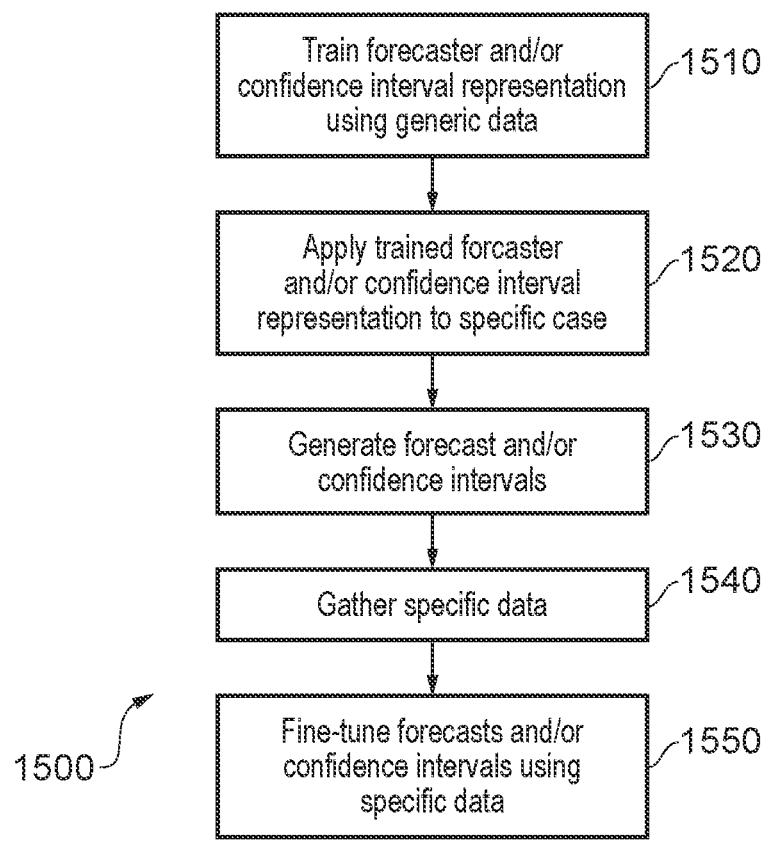
FIG. 15 shows, in the form of a flowchart, the fine-tuning process in which general forecasters are adapted to local implementations.

This process is illustrated in more detail in FIG. 15 in the form of a flowchart 1500. The process starts at step 1510 where a forecaster and/or confidence interval representation are trained using generic data. Then, at a step 1520, the trained forecaster and/or confidence interval representation are applied to a specific case (in an implementation phase). Forecasts and/or confidence intervals are then generated for the specific case using the forecaster/confidence interval representation that have been trained on general data at step 1530. Specific data relating to the implementation is then gathered at step 1540. Finally, at step 1550, the forecasts and/or confidence intervals are fine-tuned using the specific data gathered (e.g. measured) at step 1540. In this way, the forecasts and/or confidence intervals gain the advantage of the large training process while being adaptable to considerations in the local implementation.

Figure 16:
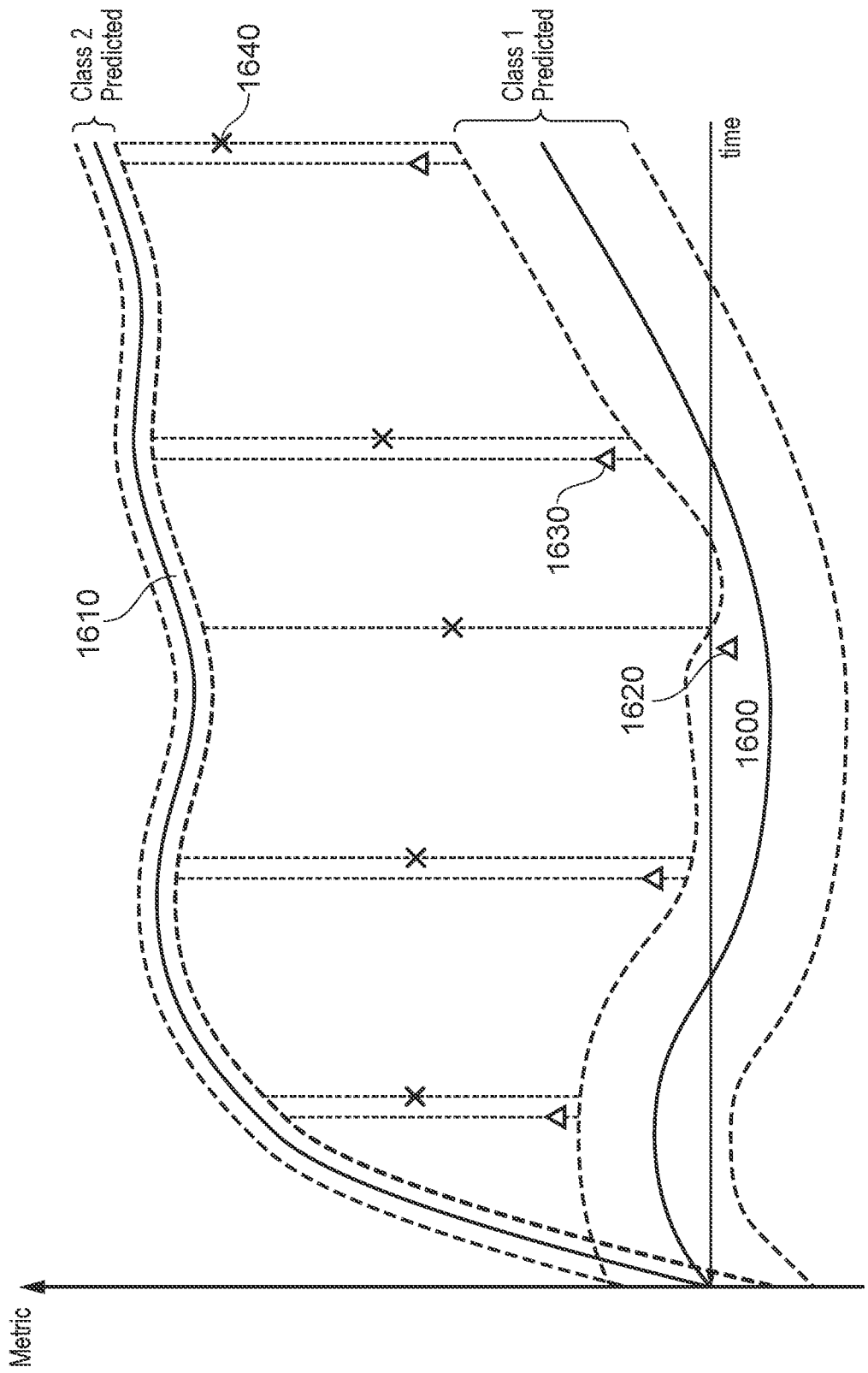
FIG. 16 illustrates a further way of representing the nature of an unknown-unknown data point.

FIG. 16 illustrates a further way of representing the nature of an unknown-unknown data point. This technique is usable with any of the techniques previously described and makes used of the distance circuitry 1220 shown in the example of FIG. 12 (although this circuitry could be applied to the previous examples of data processors described earlier). FIG. 16 shows confidence interval areas for a first class (class 1) 1600 and a second class (class 2) 1610. For each new measurement or measurements within a window (shown as triangles or crosses) a "fuzzy" distance can be calculated to each confidence interval 1600, 1610. There are a number of techniques that can be used to do this. However, in some examples, a simple Euclidian distance from the curves can be measured or estimated, with a negative measurement indicating a value inside the confidence interval and a positive value indicating a measurement outside it).

For instance, one measurement 1620 might have a value −5 in respect of the first confidence interval 1600 and a value 80 in respect of the second confidence interval 1610, indicating that the value belongs inside class 1. A second measurement 1630 might have a value 7 in respect of the first confidence interval 1600 and a value 70 in respect of the second confidence interval 1610. Finally, a third measurement 1640 might have a value 70 in respect of the first confidence interval 1600 and a value 40 in respect of the second confidence interval 1610. One might consider any data point 1630, 1640 with only positive values to be unknown-unknowns. In some examples, the smallest such value must be above a threshold for that measurement to qualify as an unknown-unknown. Note that in some examples, negative values could simply be rounded up to 0 since it may be immaterial how solidly a measurement falls within a confidence interval beyond the fact that it falls within it.

Figure 17:
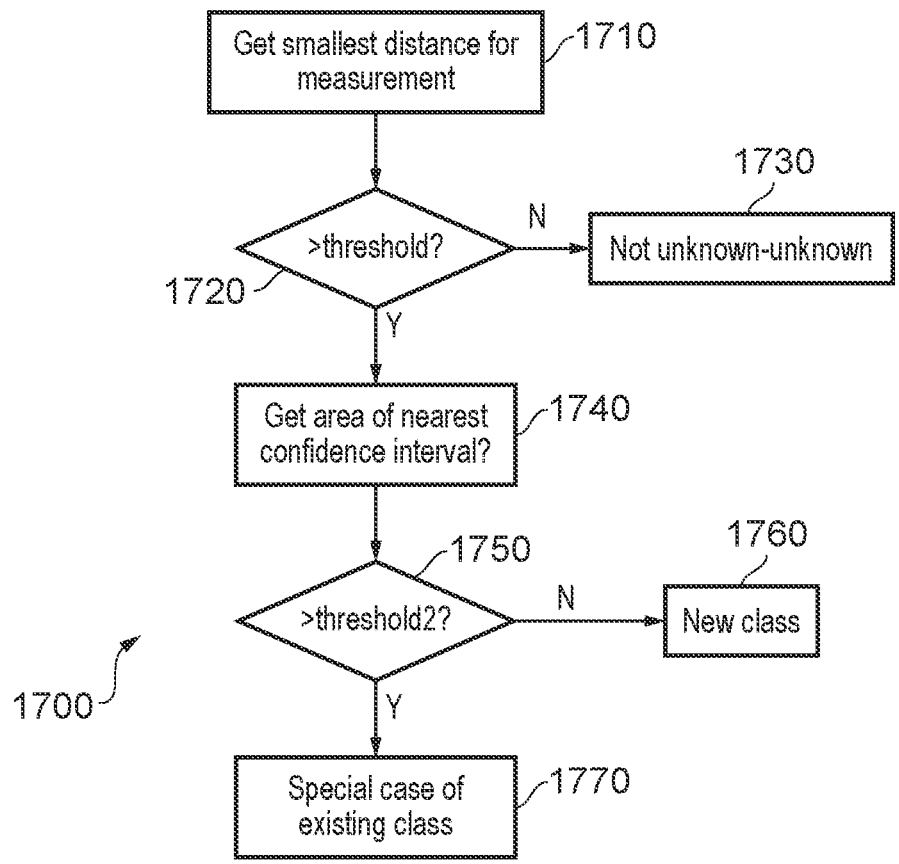
FIG. 17 illustrates, using a flowchart, different ways in which unknown-unknowns analysed using the technique shown in FIG. 16 can be characterised.

FIG. 17 illustrates, using a flowchart 1700, different ways in which unknown-unknowns analysed using the technique shown in FIG. 16 can be characterised. At a step 1710, the smallest distance between a given measurement and any of the confidence intervals is obtained. At a step 1720, it is determined whether this is greater than a threshold value. If not, then at a step 1730, the data point is considered to be either within a confidence interval, or so close to it that the data point is not considered to be an unknown unknown. Otherwise, at step 1740, the area of the nearest confidence interval is determined. At step 1750, this area is compared to a second threshold. If the area is below the second threshold, then at step 1770 the data point is considered to be a (potential) special case of that existing class, which was not considered during training of the forecaster. Otherwise, at step 1760, the data point is considered to (potentially) belong to a new class. This approach recognises that a confidence interval with a low area actually represents a high confidence and therefore a data point that is near to such a confidence interval is unlikely to be an outlier and more likely to belong to a new class). In contrast, a confidence interval with a large area represents a low confidence interval and therefore a data point that is near to such a confidence interval is more likely to be an outlier of that class.

Figure 18:
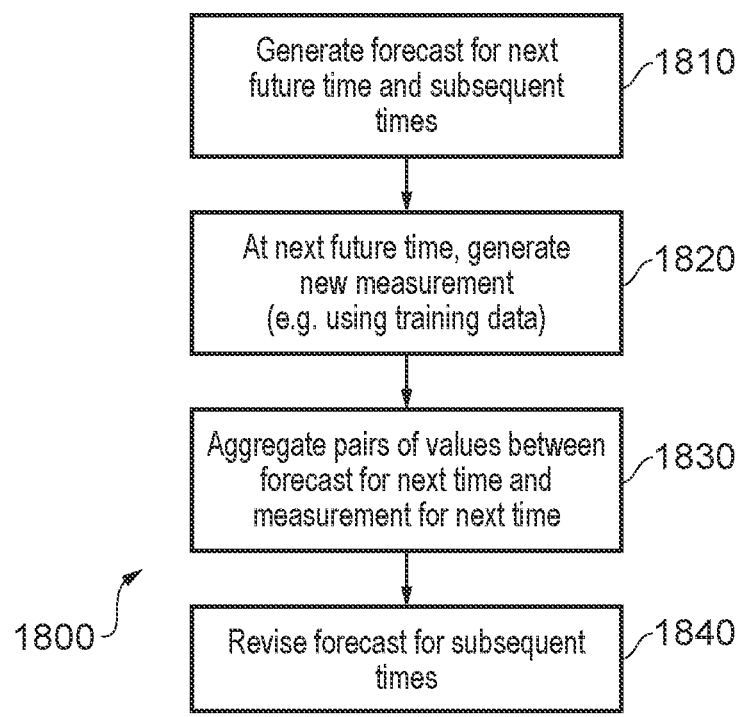
FIG. 18 shows a flowchart that illustrates a process of data processing in accordance with some of the above examples.

FIG. 18 shows a flowchart 1800 that illustrates a process of data processing in accordance with some of the above examples. At a step 1810, a forecast is generated for a next future time as well as one or more subsequent times (after the next future time). Then, at step 1820, at the next future time, a new measurement is generated. This could be using sensor data and determining a new measurement of the aspect of the system from that sensor or could simply be from additional data that was not used in training the current forecaster. At a step 1830, aggregation is performed between the forecast and the measurement. That is, pairs of values are aggregated, with a first value in each pair belonging to the measurement and a second value in each pair belonging to the forecast. Then, at step 1840, the one or more subsequent times are re-forecast, this time using the aggregation.

In the present application, the words "configured to . . . " are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments of the invention have been described in detail herein with reference to the accompanying drawings, it is to be understood that the invention is not limited to those precise embodiments, and that various changes, additions and modifications can be effected therein by one skilled in the art without departing from the scope and spirit of the invention as defined by the appended claims. For example, various combinations of the features of the dependent claims could be made with the features of the independent claims without departing from the scope of the present invention.

I claim:

1. A data processing apparatus to improve upon data comprising:
    forecast circuitry configured to generate a forecast of an aspect of a system for a next future time and for one or more subsequent future times following the next future time;
    measurement circuitry configured to generate, at the next future time, a new measurement of the aspect of the system;
    aggregation circuitry configured to produce an aggregation by aggregating
        the forecast of the aspect of the system for the next future time and
        the new measurement of the aspect of the system;
    residual calculation circuitry configured to calculate residuals of the forecast of the aspect of the system for the next future time and for the one or more subsequent future times following the next future time; and
    confidence interval generation circuitry configured to generate, for each forecast of the aspect of the system and for the one or more subsequent future times following the next future time, confidence intervals based on the residuals;
    wherein the forecast circuitry is configured to update the forecast of the aspect of the system for the one or more subsequent future times using the aggregation; and
    wherein the confidence intervals are generated so as to encompass forecasts whose residuals fall within a predefined percentile.

2. The data processing apparatus according to claim 1, wherein
    the aggregation is an average between the forecast of the aspect of the system for the next future time and between the new measurement of the aspect of the system.

3. The data processing apparatus according to claim 1, wherein
the aggregation is a weighted average between the forecast of the aspect of the system for the next future time and between the new measurement of the aspect of the system; and
each of weights applied to the forecast of the aspect of the system for the next future time and between the new measurement of the aspect of the system are different and non-zero.

4. The data processing apparatus according to claim 1, wherein
the aggregation is a weighted average between the forecast of the aspect of the system for the next future time and between the new measurement of the aspect of the system; and
each of weights applied to the forecast of the aspect of the system for the next future time and between the new measurement of the aspect of the system are different, and greater than zero.

5. The data processing apparatus according to claim 1, wherein
the next future time and each of the subsequent future times are windows of time.

6. The data processing apparatus according to claim 5, wherein
the measurement circuitry is configured to generate, at the next future time, a plurality of new measurements of the aspect of the system including the new measurement;
the aggregation circuitry is configured to produce the aggregation by aggregating corresponding pairs of values; and
each of the pairs of values has a first value associated with the forecast of the aspect of the system for the next future time and a second value associated with the new measurement of the aspect of the system.

7. The data processing apparatus according to claim 1, comprising:
circular buffer circuitry to store the forecast of the aspect of the system for the next future time and for the one or more subsequent future times following the next future time.

8. The data processing apparatus according to claim 7, wherein
the aggregation circuitry is configured to replace the forecast of the aspect of the system for the next future time with the aggregation.

9. The data processing apparatus according to claim 1 comprising:
min-sketch circuitry configured to perform min-sketch using the residuals to approximate the predefined percentile.

10. The data processing apparatus according to claim 1, wherein
the forecast circuitry is configured to generate the forecast for the next future time and for the one or more subsequent future times following the next future time, for each of a plurality of classes.

11. The data processing apparatus according to claim 10, comprising:
distance circuitry configured to determine a measurement of distance between the new measurement and the confidence interval for each of the plurality of classes, wherein
the measurement is lower when the new measurement is nearer or within the confidence interval and higher when the new measurement is further or outside the confidence interval.

12. The data processing apparatus according to claim 11, comprising:
unknown-unknown circuitry configured to label the new measurement as an unknown-unknown in response to the measurement of the distance between the new measurement and the confidence interval for each of the plurality of classes being above a threshold.

13. The data processing apparatus according to claim 12, wherein
the distance circuitry is configured to calculate the area encompassed by each confidence interval.

14. The data processing apparatus according to claim 13, wherein
the unknown-unknown circuitry is configured to label the new measurement, which is an unknown-unknown, as belonging to an unknown new class other than the classes in response to the area being above a threshold value.

15. The data processing apparatus according to claim 13, wherein
the unknown-unknown circuitry is configured to label the new measurement, which is an unknown-unknown, as a special case of one of the classes in response to the area being below a threshold value.

16. The data processing apparatus according to claim 1, wherein
the new measurement of the aspect of the system is part of a set of training data.

17. A data processing method to improve upon data of a system comprising:
generating a forecast of an aspect of the system for a next future time and for one or more subsequent future times following the next future time;
generating, at the next future time, a new measurement of the aspect of the system;
producing an aggregation by aggregating
the forecast of the aspect of the system for the next future time and
the new measurement of the aspect of the system;
calculating residuals of the forecast of the aspect of the system for the next future time and for the one or more subsequent future times following the next future time;
generating, for each forecast of the aspect of the system and for the one or more subsequent future times following the next future time, confidence intervals based on the residuals; and
revising the forecast of the aspect of the system for the one or more subsequent future times using the aggregation;
wherein the confidence intervals are generated so as to encompass forecasts whose residuals fall within a predefined percentile.

18. A non-transitory computer-readable medium to store computer-readable code for fabrication of a data processing apparatus to improve upon data comprising:
forecast circuitry configured to generate a forecast of an aspect of a system for a next future time and for one or more subsequent future times following the next future time;
measurement circuitry configured to generate, at the next future time, a new measurement of the aspect of the system; aggregation circuitry configured to produce an aggregation with: by aggregating the forecast of the aspect of the system for the next future time and the new measurement of the aspect of the system;

residual calculation circuitry configured to calculate residuals of the forecast of the aspect of the system for the next future time and for the one or more subsequent future times following the next future time; and confidence interval generation circuitry configured to generate, for each forecast of the aspect of the system and for the one or more subsequent future times following the next future time, confidence intervals based on the residuals, wherein the forecast circuitry is configured to update the forecast of the aspect of the system for the one or more subsequent future times using the aggregation, and wherein the confidence intervals are generated so as to encompass forecasts whose residuals fall within a predefined percentile.

* * * * *